United States Patent [19]
Rubin et al.

[11] Patent Number: 5,700,675
[45] Date of Patent: Dec. 23, 1997

[54] PROTEIN KINASE REQUIRED FOR RAS SIGNAL TRANSDUCTION

[75] Inventors: Gerry Rubin, Berkeley; Marc Therrien, Union City; Henry Chang, Berkeley; Felix Karim, El Cerrito; David Wassarman, San Francisco, all of Calif.

[73] Assignee: Regents of the University of California, Oakland, Calif.

[21] Appl. No.: 571,758

[22] Filed: Dec. 13, 1995

[51] Int. Cl.$^6$ .............................. C12N 9/12; C12P 21/06; C07K 1/00; C07H 21/04
[52] U.S. Cl. ............. 435/194; 435/69.1; 435/252.3; 435/320.1; 530/350; 536/23.1; 536/23.2; 536/23.5
[58] Field of Search .................... 435/194, 15, 69.1, 435/252.3, 320.1; 530/350; 536/23.1, 23.5; 424/94.5

[56] References Cited

PUBLICATIONS

Yao et al, 1995, Nature 378, 307–310; Phosphorylation of Raf by ceramide–activated protein kinase.

Dent et al., 1995, Science 268, 1902–1906; Reversal of Raf–1 Activation by Purified and Membrane-associated Protein Phosphatases.

Dent and Sturgill, 1994, PNAS USA 91, 9544–9548; Activation of (His)6–Raf–1 in vitro by partially purified plasma membranes from v–Ras–transformed and serum–stimulated fibroblasts.

Daum et al., 1994, TIBS 19, 474–480; The ins and outs of Raf kinases.

McCormick, 1994, TICB 4, 347–350; Raf: the Holy Grail of Ras Biology.

Downward et al. (1995). Cell 83: 831–834, Dec. 15, 1995.

*Primary Examiner*—Robert A. Wax
*Assistant Examiner*—Tekchand Saidha
*Attorney, Agent, or Firm*—Richard Aron Osman

[57] ABSTRACT

The kinase suppressor of Ras (Ksr), a novel protein kinase involved in the regulation of cell growth and differentiation, provides an important target for therapeutic intervention. The subject compositions also include nucleic acids which encode a Ksr kinase, and hybridization probes and primers capable of hybridizing with a Ksr gene. Such probes are used to identify mutant Ksr alleles associated with disease. The invention includes methods, including phosphorylation and binding assays, for screening chemical libraries for lead compounds for a pharmacological agent useful in the diagnosis or treatment of disease associated Ksr activity or Ksr-dependent signal transduction.

7 Claims, No Drawings

5,700,675

PROTEIN KINASE REQUIRED FOR RAS SIGNAL TRANSDUCTION

The research carried out in the subject application was supported in part by grants from the National Institutes of Health. The government may have rights in any patent issuing on this application.

INTRODUCTION

1. Field of the Invention

The field of the invention is a protein kinase required for Ras signal transduction and its use in pharmaceutical screens.

2. Background

Ras plays a crucial role in diverse cellular processes, such as proliferation and differentiation, where it functions as a nodal point transmitting signals originating from receptor tyrosine kinases (RTKs) to a variety of effector molecules (reviewed in McCormick, 1994a; van der Geer et al., 1994; Burgering and Bos, 1995). Ras activation, which involves a switch from an inactive GDP-bound to an active GTP-bound state, is promoted by a guanine nucleotide-exchange factor. Upon RTK activation, the exchange factor is recruited by an SH2/SH3 domain-containing adaptor molecule to the RTK at the plasma membrane where it can contact and activate Ras. GTP-bound Ras then transmits the signal to downstream effector molecules.

The protein serine/threonine kinase Raf has been identified as a major effector of Ras (reviewed in Daum et al., 1994; McCormick, 1994b). Upon Ras activation, Raf is recruited to the plasma membrane by a direct interaction with Ras, where it is subsequently activated by an unknown mechanism. Raf activation initiates an evolutionarily conserved pathway involving two other kinases, MEK (MAPK Kinase) and MAPK (Mitogen-Activated Protein Kinase) that convey signals to the nucleus through a directional series of activating phosphorylations (reviewed in Marshall, 1994). Although this model for Ras-dependent signal transduction is well-supported, there are still major issues that remain poorly understood. One of them is the mechanism by which Raf is activated. Recent evidence suggests that once recruited to the plasma membrane Raf is activated by phosphorylation (Dent and Sturgill, 1994; Dent et al., 1995). However, a candidate kinase(s) has yet to be identified. Another unresolved issue is the nature of other Ras effectors as well as the pathways they control. Although Raf is clearly a major Ras target, it can not account for all of the cellular responses mediated by Ras (for example see White et al., 1995).

Ectopic expression of an activated Ras1 allele, Ras1$^{V12}$, in the developing Drosophila eye transforms non-neuronal cone cells into R7 photoreceptor cells (Fortini et at., 1992). Similar results are obtained by expression of an activated Drosophila Raf allele, D-Raf$^{Tor4021}$ (Dickson et al., 1992). We carried out a genetic screen designed to isolate mutations that modify the signaling efficiency of Ras 1$^{V12}$. Most mutations that decreased the signaling efficiency of Ras1$^{V12}$ also decreased the efficiency of D-Raf$^{Torso4021}$ signaling. However, two groups of mutations were identified that did not alter D-Raf$^{Torso4021}$ signaling. We disclose here the characterization of their respective loci. The Suppressor of Ras1 2-2 (SR2-2) locus encodes a protein homologous to the catalytic subunit of the prenylation enzyme type I geranylgeranyl transferase. We have renamed this locus βGGT-I. The second locus, SR3-1, encodes a novel protein kinase distantly related to Raf kinase members. Based on its sequence and the ability of mutants to reduce Ras 1-mediated signaling, we renamed this locus kinase suppressor of ras (ksr). In addition to its function in the Sevenless RTK pathway, we show that ksr is also required for signaling by the Torso RTK. We have isolated mouse and human homologs of ksr. Together, these data indicate that Ksr is an evolutionarily conserved component of the Ras signaling pathway. As such, the human Ksr provides an important target for pharmaceutical intervention.

Relevant Literature

Recent reports on Raf activation include Dent and Sturgill, 1994; Dent et al., 1995; White et al., 1995, Yao et al, 1995; and a recent review by Marshall, 1994.

SUMMARY OF THE INVENTION

The invention provides methods and compositions relating to a novel protein kinase involved in the regulation of cell growth and differentiation: kinase suppressor of Ras (Ksr). As such, the kinase provides an important target for therapeutic intervention. The subject compositions also include nucleic acids which encode a Ksr kinase, and hybridization probes and primers capable of hybridizing with a Ksr gene. Such probes are used to identify mutant Ksr alleles associated with disease.

The invention includes methods for screening chemical libraries for lead compounds for a pharmacological agent useful in the diagnosis or treatment of disease associated Ksr activity or Ksr-dependent signal transduction. In one embodiment, the methods involve (1) forming a mixture comprising a Ksr, a natural intracellular Ksr substrate or binding target such as the 14-3-3 gene product, and a candidate pharmacological agent; (2) incubating the mixture under conditions whereby, but for the presence of said candidate pharmacological agent, said Ksr selectively phosphorylates said substrate or binds said binding target al a control rate; and (3) detecting the presence or absence of a change in the specific phosphorylation of said substrate by said Ksr or phosphorylation or binding of said Ksr to said binding target, wherein such a change indicates that said candidate pharmacological agent is a lead compound for a pharmacological agent capable of modulating Ksr function.

DETAILED DESCRIPTION OF THE INVENTION

A Drosophila melanogaster, a Drosophila virilis, a murine and a human ksr encoding sequence are set out in SEQ ID NO: 1, 3, 5 and 7, respectively. A Drosophila melanogaster, a Drosophila virilis, a murine and a human ksr protein sequence are set out in SEQ ID NO: 2, 4, 6 and 8, respectively. Ksr proteins necessarilyinclude a disclosed ksr kinase domain. Hence, Ksr proteins include deletion mutants of natural ksr proteins retaining the ksr kinase domain.

Natural nucleic acids encoding ksr proteins are readily isolated from cDNA libraries with PCR primers and hybridization probes containing portions of the nucleic acid sequence of SEQ ID NO: 1, 3, 5 and 7. Preferred ksr nucleic acids are capable of hybridizing with one of these sequences under low stringency conditions defined by a hybridization buffer consisting essentially of 1% Bovine Serum Albumin (BSA); 500 mM sodium phosphate (NaPO$_4$); 1 mM EDTA; 7% SDS at a temperature of 42° C. and a wash buffer consisting essentially of 2×SSC (600 mM NaCl; 60 mM Na Citrate); 0.1% SDS at 50° C.; more preferably under low stringency conditions defined by a hybridization buffer consisting essentially of 1% Bovine Serum Albumin (BSA); 500 mM sodium phosphate (NaPO4); 15% formamide; 1 mM EDTA; 7% SDS at lo a temperature of 50° C. and a wash buffer consisting essentially of 1×SSC (300 mM NaCl; 30 mM Na Citrate); 0.1% SDS at 50° C.; most preferably under low stringency conditions defined by a hybridization buffer consisting essentially of 1% Bovine Serum Albumin (BSA); 200 mM sodium phosphate (NaPO4); 15% formamide; 1 mM EDTA; 7% SDS at a temperature of 50° C. and a wash buffer consisting essentially of 0.5×SSC (150 mM NaCl; 15 mM Na Citrate); 0.1% SDS at 65° C.

The subject nucleic acids are recombinant, meaning they comprise a sequence joined to a nucleotide other than that to which sequence is naturally joined and isolated from a natural environment. The nucleic acids may be part of Ksr-expression vectors and may be incorporated into cells for expression and screening, transgenic animals for functional studies (e.g. the efficacy of candidate drgs for disease associated with expression of a Ksr), etc. These nucleic acids find a wide variety of applications including use as templates for transcription, hybridization probes, PCR primers, therapeutic nucleic acids, etc.; use in detecting the presence of Ksr genes and gene transcripts, in detecting or amplifying nucleic acids encoding additional Ksr homologs and structural analogs, and in gene therapy applications, e.g. using antisense nucleic acids or ribozymes comprising the disclosed Ksr sequences or their complements or reverse complements.

The invention also provides Ksr-specific binding reagents such as antibodies. Such reagents find a wide variety of application in biomedical research and diagnostics. For example, antibodies specific for mutant Ksr allele-products are used to identify mutant phenotypes associated with pathogenesis. Methods for making allele-specific antibodies are known in the art. For example, an mKsr-specific antibody was generated by immunizing mice with a unique N-terminal mKsr peptide (residues 118–249) GST fusion.

The invention provides efficient methods of identifying pharmacological agents or lead compounds for agents active at the level of a Ksr modulatable cellular function, particularly Ksr mediated signal transduction. For example, we have found that a binding complex comprising Ksr, 14-3-3 and Raf exists in stimulated cells; modulators of the stability of this complex effect signal transduction. Generally, the screening methods involve assaying for compounds which interfere with a Ksr activity such as kinase activity or target binding. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. Target therapeutic indications are limited only in that the target cellular function be subject to modulation, usually inhibition, by disruption of the formation of a complex comprising Ksr and one or more natural Ksr intracellular binding targets including substrates or otherwise modulating Ksr kinase activity. Target indications may include infection, genetic disease, cell growth and regulatory or immunologic dysfunction, such as neoplasia, inflammation, hypersensitivity, etc.

A wide variety of assays for binding agents are provided including labeled in vitro kinase assays, protein—protein binding assays, immunoassays, cell based assays, etc. The Ksr compositions used in the methods are recombinantly produced from nucleic acids having the disclosed Ksr nucleotide sequences. The Ksr may be part of a fusion product with another peptide or polypeptide, e.g. a polypeptide that is capable of providing or enhancing protein—protein binding, stability under assay conditions (e.g. a tag for detection or anchoring), etc.

The assay mixtures comprise one or more natural intracellular Ksr binding targets including substrates, such as the 14-3-3 gene product, or, in the case of an autophosphorylation assay, the Ksr itself can function as the binding target. A Ksr-derived pseudosubstrate may be used or modified (e.g. A to S/T substitutions) to generate effective substrates for use in the subject kinase assays as can synthetic peptides or other protein substrates. Generally, Ksr-specificity of the binding agent is shown by kinase activity (i.e. the agent demonstrates activity of an Ksr substrate, agonist, antagonist, etc.) or binding equilibrium constants (usually at least about $10^6 \, M^{-1}$, preferably at least about $10^8 \, M^{-1}$, more preferably at least about $10^9 \, M^{-1}$). A wide variety of cell-based and cell-free assays may be used to demonstrate Ksr-specific binding; preferred are rapid in vitro, cell-free assays such as mediating or inhibiting Ksr-protein binding, phosphorylation assays, immunoassays, etc.

The assay mixture also comprises a candidate pharmacological agent. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like salts, buffers, neutral proteins, e.g. albumin, detergents, etc. which may be used to facilitate optimal binding and/or reduce non-specific or background interactions, etc. Also, reagents that otherwise improve the efficiency of the assay, such as protease inhibitors, nuclease inhibitors, antimicrobial agents, etc. may be used.

In a preferred in vitro, binding assay, a mixture of a protein comprising at least one of the conserved Ksr domains, including CA1, CA2, CA3, CA4 and the kinase domain (see Table 1), one or more binding targets or substrates and the candidate agent is incubated under conditions whereby, but for the presence of the candidate pharmacological agent, the Ksr specifically binds the cellular binding target al a first binding affinity or phosphorylates the substrate at a first rate. After incubation, a second binding affinity or rate is detected. Detection may be effected in any convenient way. For cell-free binding assays, one of the components usually comprises or is coupled to a label. The label may provide for direct detection as radioactivity, luminescence, optical or electron density, etc. or indirect detection such as an epitope tag, an enzyme, etc. A variety of methods may be used to detect the label depending on the nature of the label and other assay components. For example, the label may be detected bound to the solid substrate or a portion of the bound complex containing the label may be separated from the solid substrate, and thereafter the label detected.

The following experiments and examples are offered by way of illustration and not by way of limitation.

EXPERIMENTAL

Mutations in the SR2-2 and SR3-1 loci suppress the eye phenotype of activated Ras 1 but not that of activated D-Raf.

Ectopic expression of activated Ras 1 (Ras $1^{V12}$) under control of sevenless (sev) promoter/enhancer sequences (sev-Ras1$^{V12}$) transforms cone cells into R7 photoreceptor cells (Fortini et al., 1992). These extra R7 cells disorganize the ommatidial array, which causes a roughening of the external eye surface. The severity of eye roughness appears proportional to the strength of Ras1$^{V12}$-mediated signaling since two copies of the transgene produce a much more disrupted eye than one copy. We took advantage of this sensitized system to conduct a screen for mutations that reduce (suppressors) or increase (enhancers) the degree of eye roughness. We reasoned that a two-fold reduction in the dose of a gene (by mutating one of its two copies) that functions downstream of Ras 1 should dominantly alter signaling strength which in turn should visibly modify the roughness of the eye. Based on this assumption, we screened ~200,000 EMS- and ~650,000 X-ray-mutagenized progeny for dominant modifiers of the Ras1$^{V12}$-mediated rough eye phenotype. 18 complementation groups of suppressors with multiple alleles and 13 complementation groups of enhancers of sev-Ras1$^{V12}$ were isolated.

To characterize further the various groups of suppressors, we tested their ability to suppress dominantly the extra R7 cell phenotype caused by overexpression of an activated Drosophila Raf allele (sE-Raf$^{Tor4021}$). Since Raf functions directly downstream of Ras, we expected most of our suppressor groups to modify similarly the sE-Raf$^{Tor4021}$ phenotype. Interestingly, two recessive lethal suppressor groups, SR2-2 and SR3-1 did not reduce the number of extra R7 cells produced by D-Raf$^{Tor4021}$ expression. Scanning electron micrographs of adult eyes illustrate the suppressor phenotypes of one SR3-1 allele. Similar results were obtained with multiple SR2-2 and SR3-1 alleles. We also monitored the suppression of extra R7 cells by counting the number of R7 photoreceptors in cross-sections of adult fly retinae. In wild-type there is one R7 cell per ommatidium, whereas in sev-Ras1$^{V12}$/+ flies we observed 2.3 (n=437) R7 cells per ommatidium. This number was reduced to 1.2 (n=481) R7 cells per ommatidium in sev-Ras1$^{V12}$/+; SR3-1$^{S-638}$/+ flies. In sE-Raf$^{Tor4021}$/+ flies, 2.3 (n=302) R7 cells per ommatidium were observed. However, this number remained at 2.3 (n=474) in sE-Raf$^{Tor4021}$/+; SR3-1$^{S-638}$/+ flies reflecting the inability of SR3-1 mutations to alter sE-Raf$^{Tor4021}$ signaling strength. Targeting of Ras1$^{V12}$ to the plasma membrane by myristylation distinguishes SR2-2 from SR3-1.

Prenylation of the C-terminal CAAX box (C=cysteine, A=aliphatic residue, X=any amino acid) is the major post-translational modification specific to all Ras-like GTPases. When the residue at position "X" is a leucine, as in Ras 1, a geranylgeranyl group is added by a type I geranylgeranyl transferase. The addition of this lipidic moiety is required to attach Ras to the plasma membrane (reviewed in Glomset and Farnsworth, 1994). Deletion of the CAAX box abolishes Ras function (Willumsen et al., 1984; Kato et al., 1992), however its activity can be restored if it is brought to the membrane by another localization signal, such as a myristyl group (Buss et al., 1989).

One possibility to account for the ability of a mutant to suppress sev-Ras1$^{V12}$ but not sE-Raf$^{Tor4021}$ is that the locus encodes an enzyme that is required for the membrane localization of Ras 1. Consequently, mutations in this locus would not affect D-Raf$^{Tor4021}$. To directly test this possibility, we asked if SR2-2 or SR3-1 alleles could suppress activated Ras 1 if it is targeted to the membrane by an alternative mechanism. We targeted Ras1$^{V12}$ to the membrane by fusing the first 90 amino acids of Drosophila Src kinase (D-Src; Simon et al., 1985), which contains a myristylation signal, to Ras 1$^{V12}$ deleted of its CAAX box (sev-Src90Ras1$^{V12\Delta CAAX}$). While the CAAX box-deleted Ras1$^{V12}$ is inactive, Src90Ras1$^{V12\Delta CAAX}$ produces the same phenotype as Ras1$^{V12}$; that is, it generates extra R7 cells and disrupts the ommatidial array.

We crossed sev-Src90Ras1$^{V12\Delta CAAX}$ flies to SR2-2 and SR3-1 alleles and analyzed the rough eye phenotype. SR2-2$^{S-2110}$ did not suppress the rough eye phenotype while SR3-1$^{S-638}$ suppressed the rough eye phenotype and the production of extra R7 cells. These observations indicate that SR2-2 is involved in prenylation of Ras 1 while SR3-1 encodes a component of the Ras 1 pathway that is not involved in the process of Ras1 membrane localization.

The SR2-2 locus encodes the Drosophila homolog of the β-subunit of type I geranylgeranyl transferase.

The SR2-2 locus was meiotically mapped to 2-15 (cytological position 25B-C), based on the ability of different mutant alleles to suppress sev-Ras1$^{V12}$. One of the seven recessive lethal SR2-2 alleles recovered contains an X-ray-induced inversion (SR2-2$^{S-2126}$) with a breakpoint at 25B4-6. Genomic DNA spanning this breakpoint was isolated and used to screen a Drosophila eye-antennal imaginal disc cDNA library (see Experimental Procedures). A single class of cDNAs (ranging in size from 0.8 to 1.6 kb) defining a transcription unit disrupted by the inversion present in SR2-2$^{S-2126}$, was identified and characterized. Conceptual translation of the longest open reading frame (ORF) defined by these cDNAs predicts a protein of 395 amino acids. Determination of the gene structure by sequencing the corresponding genomic region revealed four exons with the first in-frame methionine located at the beginning of the second exon. The SR2-2$^{S-2126}$ inversion breakpoint maps to the 5'-end of the transcript. Further confirmation that this ORF corresponds to the SR2-2 gene, was provided by sequence analysis of two other mutant alleles, SR2-2$^{S-483}$ and SR2-2$^{S-2554}$, both of which have small deletions that remove the first exon and part of the 5' regulatory sequences. A search of the current protein databases with this ORF indicated that the SR2-2 gene encodes the Drosophila homolog of the catalytic β-subunit of type I geranylgeranyl transferase (βGGT-I) (Marshall, 1993). Sequence alignment with the human and the yeast *S. pombe* βGGT-I proteins shows a high degree of evolutionary conservation. The human sequence is 44% identical (69% similar) to the Drosophila sequence throughout the entire ORF while the yeast sequence is 36% identical (57% similar) to the Drosophila protein. We therefore renamed this locus, βGGT-I.

The SR3-1 locus encodes a novel protein kinase.

The ability of SR3-1 mutant alleles to suppress the sev-Ras1$^{V12}$ phenotype was meiotically mapped to 3-47.5, which corresponds to a region near the chromocenter of the third chromosome. The map position was further refined by showing that SR3-1 meiotically maps between two P-elements inserted at 82F8-10 and 83A5-6, respectively. X-ray-induced chromosomal deletions were generated by selecting w revertants of one of the P-element insertions. One such deletion, Df(3R)e1025-14, which removes the chromosomal region from 82F8-10 to 83A1-3, complemented the SR3-1-associated lethality. Taken together, these results indicated that the SR3-1 locus lies between 83A1-3, the distal breakpoint of Df(3R)e1025-14, and 83A5-6, the insertion site of P[w$^+$]5E2.

Five overlapping cosmids which cover this chromosomal region were recovered by chromosome walking. To identify restriction site polymorphisms that might have been induced in the SR3-1 alleles, these cosmids were used to probe genomic DNA blots prepared from 9 independent X-ray-induced SR3-1 alleles. Cosmid III revealed polymorphisms in a BamHI restriction digest of two alleles, SR3-1$^{S-69}$ and SR3-1$^{S-511}$. No other cosmid revealed polymorphisms in the 9 tested alleles. A 7 kb SacII genomic fragment which spans the polymorphic BamHI fragments was introduced into the germline by P-element-mediated transformation. This genomic fragment, tested in transgenic flies, rescued both the lethality and the sev-Ras1$^{V12}$-suppression ability of three independent SR3-1 alleles. A single class of cDNAs that was totally encoded by the 7 kb genomic fragment was identified by screening a Drosophila eye-antennal imaginal disc cDNA library and sequenced. The longest cDNA clone represents a transcript of 3.6 kb which is close to the size of a full-length transcript since RNA blot analysis identified a single band of similar size. Sequence analysis of the genomic region revealed that this transcript is encoded by a single exon. Conceptual translation of the longest ORF predicts a protein of 966 amino acids. The presence of an in-frame stop codon upstream of the predicted initiating methionine indicates that this cDNA contains the complete ORF.

A search of current protein databases indicated that SR3-1 encodes a novel protein kinase. The putative catalytic domain, which is C-terminal, contains the characteristic eleven conserved sub-domains found in eukaryotic kinases (Hardie and Hanks, 1995) and is preceded by a long N-terminal region with three distinctive features: a cysteine-rich domain similar to those found in Protein Kinase C isozymes (Hubbard et al., 1991) and Raf kinases (Bruder et al., 1992); four sequences that match the consensus phosphorylation site (PXS/TP) for MAPK (Marshall, 1994); and a block of amino acids rich in serines and threonines followed by a conserved motif (FXFPXXS/T) that resembles the sequence around the Conserved Region 2 (CR2) domain of Raf kinases (Heidecker et al., 1992). Since the SR3-1 locus encodes a putative protein kinase and mutant alleles were isolated as suppressors of sev-Ras1$^{V12}$, we renamed this locus kinase suppressor of ras (ksr).

Further confirmation that this gene corresponds to the ksr (SR3-1) locus was provided by sequencing three ksr alleles which revealed mutations disrupting the Ksr ORF (Table 1).

TABLE 1

Sequence comparison of the Ksr kinases.

```
                                                                                                          GS (S-548)
                                                      CA1                                                    ▲
Dm Ksr  . ms s NNNa . . . . . . p As APDTgs T . . nAnDPI SGgLSVDsnl vi qdmi dl sanhl egl rt qcaI sSt l t qqeei rcl eskl vry f sel l l AkMf l neri pangl Vph. . Tt gnel r qwl r vvg  112
Dv Ksr  . ms s SAAa QLTAPpVsNSNSSsS. . nNnTTTTAs. . . Esnl Ii qdmi dl sanhl egl rt qcaTsAt l t qqei r cl eskl vry f sel l l TkTl neri pangl LphHQAt gnel r qwl r vvg  116
mKsr-1  MDRAAL Ra AAMGE KKE GGGGg AA. . ADGGAGAAVS RAL QQCGQ L qKLi dl sI sI Rgl rt Kc SVs NDI t qqeI rTl eAkl vKyf CKQQQSkLSVTPSDRTAEI NSYPR. . . . FSDwl YI FN  115
hKsr-1  RAAL RS AAL GE KKE GGGGg DAAI AE GGAGAAAS RTL QQCGQ L qKLi dl sI sI Rgl rt Kc VVs NDI t qqei rTl eAkl vRyi CKQRQCkLSVAPGERTPEI NSYPR. . . . FSDwI YI FN  117

Dm Ksr  l s QGTl Tacl arl l t t l eqSl Rl sdeel Rql l aDSPs QReeeel rrl l t Ramqnl r kcme Sl EsG . . . . . . . . . . . . . . . . . . . . . i gl gNnst aspr Thhr qhGVKGKns  229
Dv Ksr  l s PESl Nacl arl l t t l eqTl Ql sdeel Kql l aHNSsTQLDeel rrl l t Kamhl nl r kcme Tl DsS t a. asnNd peq wh wds wdr . . . pThl hr gsVgn. . . . . . . . . . . . i gl gNnst aspr Thhr qhGVKGKns  235
mKsr-1  VRPEVVQEI PQEl . t l DALl EMDEAKAKEMI RRWGASTeeCS. . . . . . . . . . . . . . . . . . Ga Vas nVd peq wh wds wdr PHpHhMhr gs I gn. . . . . . . . . i gl gLsSaspr Ahhr qhQHQHAns  213
hKsr-1  VRPEVVQEI PRDl . t l DALl EMNEAKVKETi RRCGASGDeCG. . . . . . . . . . . . . . . . . . t GLGGEHKMDS GWS STDAr DSSLGPPMDM. SS. . . . . . . . . Lg RAGAst QCpr S. . . . . . . . . . .  226
                                                                                                                                                                R1 QQALTCl RKV
                                                                                                                                                                R1 QYALTCLRKV CA2
Dm Ksr  ALANSTnFKs GRQs PSATEeLNSTQs ql t l t l t ps ppns pf t pSs gLSs sSLNgt pqr sr . . . . . . . . . sQSHVQVDGEQLAr Nr l pt dps Tdshss T. . ssdi f  336
Dv Ksr  KPKI VNnSAs SSRs. . . . . eQQPLTgs ql t l t l t ps ppns pf t pAs gTAs A. Sgt pqr sr STTTAAgt pppaKkhqt l l MHNSSAs ETALAEQPPRPr Sr l pt dps Pdshss ASssdi f  349
mKsr-1  . . . . I SVSALPASDSPVPGLSEGLSDs CI Pl HTS. . GRLTpRALHs FI TPPTTPQLRr HAKL KPPRTPppSr kVFQl l . . . . . . . . . . . . . . . . . . . . . . . . PSFpt LTRSKs hEs QL GNRi .  306
hKsr-1  . . . I SVSALPASDSPTPSFSEGLSDTCI Pl HAS. . GRLTpRALHs FI TPPTTPQLRr HTKL KPPRTPpppSr kVFQl l . . . . . . . . . . . . . . . . . . . . . . . . PSFpt LTRSKs hEs QL GNRi .  319

●
                                                                                          ●
                                                                                          ●
                                                                                          ●                CA3
Dm Ksr  vdPNTNASSGGs s s nvl MvpCs pgvGhvgmghAi khr f Tk AL gf mat . cTl cqkq Vf HRrwMkct dckyi chkscaphvpps cgl preyvDef r HI KEQg GYASLpHVhGa AkGs pLVKks  455
Dv Ksr  vd. . . . . . GGSI Ns s nvl LvpPs pgvAhvgmghTi khr f SkWF gf mat . cKI cqkqMMSHwFkct dckyi chkscaphvpps cgl pr eyvHef r QTQVGgRWD. . pAQhSSSKAs pVPRks  461
mKsr-1  DDVTPMKFELPHGs pQLVRRDI gLSVThr f DTKSWL SQV. cNVcqks MI FG. Vkc KHc RLKch NKc TKE. ApAc RI TFLPLARLr RTESVPSDI NNp VDRAaEPHFGTLPkA  415
hKsr-1  . . . . DDVs s MRFDLSHGs pQMVRRDI gLSVThr f DTKSWL SQV. cHYcqks MI FG. Vkc KHc RLKch NKc TKE. ApAc RI SFLPLTRLr RTESVPSDI NNp VDRSaEPHFGTLPkA  428
D-Raf                                                                       i kh QI I RKI Ff SLVFc EGe RRLLf TGF. Yc SQc NFRFh QRc a NRvpMLc   310
hc-Raf                                                                      t Th Nf ARKTFLKL AFc DI cqKFLLNGFr Rr c QTc Gy KFh EHc STKypTMs   184

CA4
Dm Ksr  t l gkpLHq. . . . qhgds s s pss s ct s s t ps s pal f q. . qREREI DQAGSs. . . SSANLLPTPSL GKhqPs qf nf pnvt Vt s . . . . . s GGs Gg VSl i s nepVPEQFPt APa Tang GLD. .  558
Dv Ksr  t l gkpQLqQPQLqhgds s s pss s ct s s t ps s pal f q. . qQQL QI ATPSACQPKPAPAAVAAAAATQQQq Qs qf nf pnvt Lt s NACNs NAs AAQTl i s nepQAHMATi ESTLI ngNNNSS  578
mKsr-1  LTKkE. . HPPAMN. I ds s NPs s Tt s s t ps s paPf LTSSNPSSATTPNPs PGQRD. . . . . . . . . . . sRf Sf pDI SACs QAAPLSTADSTRI . DDQpKI DVLGVHEaEEPEAGK  517
hKsr-1  LTKkE. . HPPAMNhL ds s NPs s Tt s s t ps s paPf TSSNPSSATTPPNPs PGQRDSRFNFPAAYFi hHRQqf I f pDI SAF AHAAPL PEAADgTRI . DDQpKADVLEAHEaEEPEAGK  543
```

TABLE 1-continued

Sequence comparison of the Ksr kinases.

```
Dm Ksr  ............slVssngiMSslIgsqTs..........NAsTAAtLiGslvnsTTTTSTCsffprklsTagvdktTpftseCtdthksndsdktvslsgssastdsdrtpvrVdste  655
Dv Ksr  SNNGSSANNNSSsSSsCsngiLHslTgsqVsTHSATSQVSNVSGsSSatYtSslvnsG......sffprklsNagvdktVpftseYtdthksndsdktvslsgssastdsdrtpvrLdste  692
mKsr-1  SEAEDDEEDEVDDIPss.............................................................................rRpWRG...................PlsRKas  547
hKsr-1  SEAEDD.EDEVDDIPss.............................................................................rRpWRG...................PlsRKas  572
                                                                                                          T (S-638)        (S-721)
                                                                                                            ▼                  ▼

Dm Ksr  dgdsgqwrqnsislkewdipygdlllleriggqgrfgtvhralwhgdvavkllnedylqdehmleTfrSevanfkNtrhenlvlfmgacmppylaivtslckgntlytyihqrrekfarm  775
Dv Ksr  dgdsgqwrqnsislkewdipygdlHlleriggqgrfgtvhralwhgdvavkllnedylqdehmleSfrNevanfkKtrhenlvlfmgacmppylaivtAlckgntlytyihqrrekfaum  812
mKsr-1  .........qTsVYlQewdipFEQVElGePiqggrWgRvhrGRwhgEvaIRIIEMiGHNQDh..lKLfKKevMnYRQtrhenVvlfmgacmppHiailtsFckgRtlHSFVRDPKTSLDIn  658
hKsr-1  .........qTsVYlQewdipFEQVElGePiqggrWgRvhrGRwhgEvaIRIIEMiGHNQDh..lKLfKKevMnYRQtrhenVvlfmgacmppHiailtsFckgRtlHSFVRDPKTSLDIn  683
D-Raf   DAKSsEENwNiLAEElIIGPrigSgSsfgtvYraHwhgPvPvkTlnVKTPSPAQ.lQafKNevaMLkKirhCnILlfmg..cVSKpSlaivtQWcEgSSlyKHVhVSETkfKLn  565
hc-Raf  GQRDsSYYwEiEASEVMlSTrigsSgSfgtvYKCKwhgdvavkIlKVVDPTPeQ.FQAfrNevaVLRKirhVnILlfmg..YmTKDNlaivtQWcEgSSlyKHLhVQETkfQmF  443
               I                            II                                  III                                IV                V Dm Ksr  rtlliaqqiaggmgylharEiihkdlrtknifieng.kviiitdfglfsstkllycdm...glgvphnwlcylapeliralqpEkpRgeclefPysdvysfgtvwyelicgefftfkdqpa  891
Dv Ksr  rtlliaqqiaggmgylharDiihkdlrtknifieng.kviiitdfglfsstkllycdm...glgvpQnwlcylapeliralqpCkpPgecleftSysdvysfgtvwyelicgefftfkdqpa  928
mKsr-1  KtRQiaqEIIKgmgylhaKGiVhkdlKSknVfYDng.kvVitdfglfGlSGVVREERRENQlKLShDwlcylapelVrEMIpGRDEDQ.lPfSKAAdvyAfgtvwyelQARDWPfkHqpa  776
hKsr-1  KtRQiaqEIIKgmgylhaKGiVhkdlKSknVfYDng.kvVitdfglfGlSGVVREGRRENQlKLShDwlcylapelVrEMIpGkDEDQ.lPfSKAAdvyAfgtvwyelQARDWPLkNqAa  801
D-Raf   TLIDiGRqVaqgmDylhaKNiihRdlKSNnifLHEDLSvKiGdfgl ATAKTRWSGEKQANQ...pTGSILWMapeVir.......MQeLNPYSFQsdvyAfgivMyelLABCLPYGHISN  675
hc-Raf  QLIDiaRqTaqgmDylhaKNiihRdMKSNnifLHEgLTvKiGdfgl ATVKSRWSGSQQVBQ...pTGSVLWMapeVir.......MQDNNPfSFQsdvySYgIvLyelMIgeLPYSHINN  553
                 VIa                        VIb                       VII                                VIII                     IX Dm Ksr  .esiiiwqvgr..gmkqslanlqsg..rdvkdllmlcwtyekehrpQfarllsllleh...lpkkrlarspshpvnlsrsaesvf (SEQ ID NO: 2)                      966
Dv Ksr  .esiiiwqvgr..gmkqslanlqsg..rdvkdllmlcwtyekehrpDfarllsllleh...lpkkrlarspshpvnlsrsaesvf (SEQ ID NO: 4)                      1003
mKsr-1  .eALiwqIsGEgVRRVlaSVSLg..KEvGEIlSAcwAFDLQErpSfSLFMDMeR......lpk..lNrRLshpGHFWKsaDINSSKVMPFERFGLGTLESGNPKM (SEQ ID NO: 6)  873
hKsr-1  .eASiwqIsGEgmkRVlTSVSLg..VhkdlKEvSEIlSAcwAFDLQErpSfSLFMDMeK......lpk..lNrRLshpGHFWKsaeL (SEQ ID NO: 8)                     874
D-Raf   GL.LRPDMSQVRsDARrHSkRlAEDclKyTPKDrpLfRPIlWMleNMLRTIpk..IHrsAsEp.nlTQsQLQND. (SEQ ID NO: 11)                                781
                        X hc-Raf  KDQiLFMvgrRDQiiFMvgrGY.ASPDISKIYKNCPKAMcRlVADcVKKVleErpLfPQIlsSIeLLQHSlpk..INrsAsEp.SlHrAaHTEDlNACTLTTSPRLPVF (SEQ ID NO: 12)  648
                                        XI
```

Table 1 provides a detailed comparison of the predicted amino acid sequence of Ksr kinases. Conceptual translation of the open reading frame from the longest *D. melanogaster* (Dm) Ksr cDNA is shown. The positions of mutations in three ksr alleles are indicated: S-548 is a 4 bp X-ray-induced mutation affecting two consecutive codons (CTG-CGA to AGT-GGA). S-638 is an EMS-induced allele that has two separate point mutations changing a GCC codon to GTC and GCG codon to ACG. S-721 is a frameshift mutation due to a 10 bp duplication from adjacent sequences within the codon for asparagine-727. Also shown in the alignment are the conceptual translations of the open reading frames for the Ksr genes from other species: the *D. virilis* (Dv) Ksr sequence was derived from genomic DNA, the mouse (m) Ksr-1 from a 4 kb cDNA, and the human (h) Ksr-1, deduced from three overlapping cDNA clones (the N-terminal two residues were absent from these clones so the numbering begins with the third residue). The human Ksr is present as one or more of a plurality of alternatively spliced forms, exemplified by Ksr' in the following sequence listing. The amino acid sequences (and their respective positions) for the cysteine-rich regions and the kinase domains of Drosophila (D-Raf) and human (h c-Raf) (Genbank accession number: X07181 and X03484, respectively) are presented. Residues identical to Dm Ksr are lower case. In the N-terminus of the Ksr kinases four Conserved Areas (CA1 to CA4) are boxed. CA1 is a novel domain present only in the Ksr kinases. CA2 is a proline-rich stretch that may represent an SH3-binding site (Alexandropoulos et al., 1995). CA3 is a cysteine-rich stretch, simlar to a domain found in multiple signaling molecules. This conserved sequence is also part of the CR1 domain found in Raf kinases (Bruder et al., 1992). CA4 is a long serine/threonine-rich stretch followed by a conserved motif (indicated by a dashed line). This domain resembles the region around the CR2 domain of Raf kinases (Heidecker et al., 1992). The four short thick lines overlying the sequences indicate potential sites of phosphorylation by MAPK (PXS/TP) found in Dm Ksr. The eleven conserved sub-domains characteristic of protein kinases are indicated by roman numerals below their approximate positions.

ksr$^{S-638}$ has two single amino acids changes: alanine-696 to valine and alanine-703 to threonine. The latter substitution alters a highly conserved residue within kinase sub-domain II (Hanks et al., 1988). ksr$^{S-721}$ contains a 10 bp insertion in the codon for asparagine-727 within kinase sub-domain III creating a frameshift mutation that truncates the protein at kinase sub-domain III. ksr$^{S-548}$ has a four base pair substitution that changes two consecutive amino acids in the N-terminus of the protein: leucine-50 and arginine-51 to glycine and serine, respectively. Unlike the 16 alleles recovered in the screen which were recessive lethal, ksr$^{S-548}$ produces sub-viable flies which have rough eyes (see below), indicating that it is a weak loss-of-function mutation.

Identification of Ksr homologs in other species defines a novel class of kinases related to Raf kinases.

As a first attempt to determine functionally important domains that comprise the Ksr kinase, we searched for homologs from other species. First, we isolated the complete coding region of ksr from a *Drosophila virilis* genomic library by low-stringency hybridization (see Experimental Procedures). The *D. virilis* genomic sequence revealed a single uninterrupted ORF predicting a protein of 1003 amino acids (Table 1). The *D. virilis* and *D. melanogaster* Ksr proteins are 96% identical within the kinase domain while the N-terminal region is more divergent (69% identity), although islands of high conservation are present (see Table 1).

A search of translated nucleotide databases (using the TBLASTN program; Altschul et al., 1990) identified a partial ORF derived from a mouse DNA sequence with significant blocks of similarity to the N-terminus of Ksr. This sequence, named hb, had been isolated by Nehls et al. (1994) as part of an exon-trapping strategy to establish the transcription map of a 1 Mb region around the mouse NF1 locus. To determine if the full-length hb transcript also contains a kinase domain related to Ksr, we screened a cDNA library derived from a mouse PCC4 teratocarcinoma cell line with a probe corresponding to the hb sequence (see Experimental Procedures). A 4 kb cDNA clone was isolated and encodes a protein of 873 amino acids that contains a kinase domain highly related to the Ksr kinase domain (51% identity/74% similarity; Table 1). In addition, a human fetal brain cDNA library was screened at low-stringency with the same hb probe (see Experimental Procedures). Thirteen independent cDNA clones were purified and sequenced. They represent partial transcripts ranging in size from 0.6 to 3 kb. Interestingly, they define at least three classes of N-terminal splicing variants. The predicted protein sequence derived from overlapping human cDNA clones is shown in Table 1. With the exception of the first divergent 23 amino acids, which probably represents an alternative exon, human Ksr-1 (hKsr-1) is nearly identical to mouse Ksr-1 (mKsr-1; 95% identity/99% similarity). Subsequent to this analysis, two human Expressed Sequence Tags (Genbank accession numbers: R27352 and R27353) have been reported that correspond to regions of the hKsr kinase domain.

Comparison of mammalian and Drosophila Ksr sequences showed similarity throughout the kinase domain as well as at various locations within the N-terminal region (Table 1). Sequence conservation is obvious within all sub-domains of the kinase domain. Two interesting features are present within sub-domains VIb and VIII. HRDL(K/R/A)XXN (D and N are invariant residues) is the consensus sequence corresponding to sub-domain VIb for the majority of known kinases (Hardie and Hanks, 1995). Instead of an arginine at the second position, a lysine is present for the Ksr homologs which distinguishes them from most other kinases. In addition, the amino acids N-terminal to the APE motif in sub-domain VIII, which have been implicated in substrate recognition specificity, (Hardie and Hanks, 1995) are well-conserved between the Ksr kinases of different species, but differ from those of all other kinases. One peculiarity is found in sub-domain II of the two mammalian proteins. This sub-domain has an invariant lysine residue involved in the phospho-transfer reaction that is conserved in all kinases identified thus far (Hardie and Hanks, 1995), however, both mammalian sequences have an arginine at this position (Table 1). It has been shown that mutagenesis of this lysine residue to any other residue, including arginine, abolishes catalytic function in several kinases (Hanks et al., 1988). However, the sequence conservation between the mouse and the human kinase domains indicates that these enzymes are functional.

Sub-domains VIb and VIII also contain conserved residues that often correlate with hydroxy amino acid recognition (Hanks et al., 1988). For instance, HRDLKXXN (VIb) and T/SXXY/F (VIII) motifs are indicative of Ser/Thr-kinases while HRDLR/AXA/RN (VIb) and PXXW (VIII) motifs are associated with Tyr-kinases. Based solely on these conserved residues it is not clear to which class Ksr kinases belong (Table 1). Indeed, for sub-domain VIb, the Drosophila sequences have an arginine residue at the critical position (like a Tyr-kinase), while the two mammalian sequences have a lysine residue (like a Ser/Thr-kinase). The sub-domain VIII motif for all the Ksr members is WXXY, which differs from that found in all other kinases.

In the N-terminal region, four Conserved Areas (CA1 to CA4) can be recognized (Table 1). CA1 is a stretch of 40 amino acids located at the very N-terminus of Ksr kinases and has no equivalent in the database. Its conservation and the identification of a mutation in it (ksr$^{S-548}$) indicate that it plays a role in Ksr function. CA2 is a proline-rich stretch followed by basic residues which may correspond to a class II SH3-domain binding site (PXXPXR/K; Alexandropoulos et al., 1995), although the two fly sequences diverge from the consensus by one amino acid. CA3 is a cysteine-rich domain similar to the one found in other signaling molecules, such as the CR1 domain of Raf. Finally, CA4 is rich in serines and threonines and also contains a MAPK consensus phosphorylation site.

A search of current databases indicated that the Raf kinase members are the closest relatives to the Ksr kinases based on sequence similarity within the kinase domain (e.g. 42% identity/61% similarity between the Dm Ksr and Raf kinase domains) and shared structural features in the N-terminal region (Table 1). Both the Raf and Ksr kinases have a related C-terminal 300 amino acid kinase domain, named CA5 and CR3, respectively (CR3; Heidecker et al., 1992). The spacing and sizes of the domains of the Ksr kinases are well conserved, except for the presence of an additional ~100 amino acids between the CA4 and CA5 domains of the Drosophila sequences. In addition, they both have a long N-terminal region that contains a cysteine-rich stretch followed by a serine/threonine-rich region, named CA3 and CA4 for Ksr kinases and CR1 and CR2 for Raf kinases. Ksr and Raf kinases also have distinctive features. For instance, the CA1 and CA2 regions found in Ksr kinases are absent from Raf kinases. The Ras-binding domain (RBD) found in the CR1 domain of Raf kinases (Nassar et al., 1995) is absent from Ksr kinases, which suggests that they are regulated differently. Moreover, interaction assays using the yeast two-hybrid system or bacterially-expressed fusion proteins, did not detect any interaction between Ras 1 and Ksr, while similar experiments detected an interaction between Ras 1 and the CR1 domain of D-Raf. Finally, amino acids in kinase sub-domain VIII, which are important for substrate recognition, are not conserved between Ksr and Raf kinases suggesting that these kinases have different targets. This is supported by the observation that Ksr failed to interact with Dsor1 (D-MEK) in a yeast two-hybrid assay, whereas, D-Raf and Dsor1 interacted strongly.

Ksr functions in multiple RTK pathways.

Recent evidence suggests that RTKs use a similar set of proteins to transduce their signals to the nucleus (see Background). Several lines of genetic evidence suggest that the Ksr kinase corresponds to a new component of this widely used signal transduction pathway. For instance, adult flies homozygous for the sub-viable allele ksr$^{S-548}$ have rough eyes in which ommatidia are missing both outer (R1–R6) and R7 photoreceptor cells. This suggests that, like Ras1 (Simon et al., 1991), ksr has a broader role than just specification of the R7 cell fate. Using the FLP/FRT system (Xu and Rubin, 1993), we did not recover homozygous mutant tissue for the strong allele ksr$^{S-638}$; which indicates that Ksr is required for cell proliferation or survival. In addition, except for the ksr$^{S-548}$ allele, all ksr alleles are recessive lethal and in most cases they die as third instar larvae and lack imaginal discs. This phenotype is often seen with mutations in genes required for cell proliferation (Gatti and Baker, 1989). RNA in situ hybridization showed that ksr mRNA is ubiquitously distributed and is present throughout embryogenesis, consistent with a general role for this kinase.

We directly tested whether ksr is an essential component of the Torso RTK pathway, another Drosophila RTK-dependent signal transduction cascade (reviewed in Duffy and Perrimon, 1994). Torso initiates a signal transduction cascade required for development of the anterior and posterior extremities of the embryo. As for the Sevenless RTK pathway, genetic screens aimed at elucidating this pathway have led to the identification of drk, sos, Ras1 and genes encoding the downstream cassette of kinases (Raf/MEK/MAPK) as being critical for signal propagation (reviewed in Duffy and Perrimon, 1994). This signal transduction cascade appears to control the expression pattern of two genes, tailless (tll) and huckebein (hkb) at the embryonic termini (reviewed in Duffy and Perrimon, 1994). During the cellular blastoderm stage, the posterior domain of expression of both factors depends uniquely on Torso-mediated signaling thereby providing excellent markers of Torso activity.

Embryos derived from mothers homozygous for a torso null mutation have defective termini. The posterior end is missing all structures beyond the seventh abdominal segment, while the anterior end exhibits severe head skeleton defects (reviewed in Duffy and Perrimon, 1994). Consistent with these abnormalities, aberrant expression patterns are observed for tll and hkb; that is, no tll or hkb expression is detected at the posterior end, while tll expression pattern is extended and hkb is retracted at the anterior end. Embryos derived from germlines homozygous for loss-of-function mutations in general RTK components like drk, sos, Ras1 or D-Raf show similar terminal defects, albeit to various degrees, consistent with their role in Torso RTK-mediated signaling (Hou et al., 1995).

To determine whether ksr acts in the Torso pathway, we used the FLP-FDS system (Hou et al., 1995) to generate ksr germline clones and examined the terminal structures of embryos derived from homozygous mutant oocytes. Like embryos derived from Torso mutant mothers, cuticle preparations of ksr$^{S-638}$ embryos revealed severe terminal defects. They are missing posterior structures beyond the seventh abdominal segment and have collapsed head skeletons. In addition, no tll or hkb expression is detected at the posterior end while a broader domain of tll expression and a reduced one for hkb is observed at the anterior extremity. These results indicate that ksr also functions in the Torso pathway, consistent with Ksr being a general component acting downstream of RTKs.

Activated D-Raf rescues terminal defects observed in embryos derived from germlines homozygous for ksr$^{S-638}$.

The inability of ksr mutants to suppress the sE-Raf$^{Tor4021}$ phenotype in the eye suggested that Ksr functions upstream or in parallel to D-Raf, but not downstream. To clarify where ksr functions relative to D-Raf in the Torso pathway, RNA encoding an activated form of D-Raf (Raf$^{Tor4021}$) was injected into embryos derived from germlines homozygous for ksr$^{S-638}$. If Ksr functions solely upstream of D-Raf then activated D-Raf should rescue the mutant phenotype. In contrast, if Ksr functions solely downstream of D-Raf then injection of activated D-Raf RNA should have no influence on the ksr$^{S-638}$-associated embryonic phenotype. It is also possible that rescue might be observed if Ksr functions in a pathway parallel to D-Raf and can be bypassed by activation of D-Raf to sufficiently high levels. Injection of activated D-Raf partially rescued the ksr$^{S-638}$-associated embryonic terminal defects. These results confirm that Ksr does not act downstream of D-Raf.

Experimental Procedures

Fly culture and crosses were performed according to standard procedures. Clonal analysis in the eye was performed on the ksr$^{S-638}$ allele (the strongest suppressor of sev-Ras1$^{V12}$ among the ksr alleles) using the FLP/FRT system (Xu and Rubin, 1993).

ksr$^{S-638}$ germline clones were generated as described in Hou et al. (1995). Cuticle preparation of embryos was performed as described in Belvin et al. (1995). In situ hybridization was performed according to Dougan and DiNardo (1992) using digoxigenin-labelled RNA probes. Injection of embryos was performed as described in Anderson and Nüsslein-Volhard (1984). An in vitro trancription kit (Promega) was used to synthesize activated D-Raf RNA from the Raf$^{Tor4021}$ DNA template (Dickson et al., 1992).

Scanning electron microscopy was performed as described by Kimmel et al. (1990). Fixation and sectioning of adult eyes were performed as described by Tomlinson and Ready (1987).

The βGGT-I locus was recovered from a chromosome walk initiated by screening a cosmid library (Tamkun et al., 1992) with a genomic fragment flanking a P-element [1(2)05714] inserted at 25B4-6 (Karpen and Spradling, 1992; Berkeley Drosophila Genome Project, pers. comm.). A 1.7 kb Spe1-Sph1 genomic fragment spanning the S-2126 allele inversion breakpoint was used to screen a Drosophila eye-antennal imaginal disc cDNA library in λgt10. Sixteen related cDNA clones were isolated from ~700,000 pfu screened.

The ksr gene was isolated from a chromosome walk. Genomic blot analysis of X-ray-induced ksr alleles was performed according to standard procedures (Sambrook et al., 1989). The 2.9 kb and 2.2 kb BamHI fragments from cosmid III identified polymorphisms in the S-69 and S-511 alleles, respectively. A 7 kb EcoRI genomic fragment encompassing all of the 2.9 kb BamHI fragment and part of the 2.2 kb BamHI fragment was used along with the 2.2 kb BamHI fragment to screen ~700,000 phage from a Drosophila eye-antennal imaginal disc cDNA library in λgt10. Seven related cDNA clones were isolated and characterized by sequencing.

A *D. virilis* genomic library was screened at reduced stringency using the Dm Ksr kinase domain as a probe. In brief, filters were hybridized in 5×SSCP; 10×Denhart; 0.1% SDS; 200 µg/ml sonicated salmon sperm DNA at 42° C. for 12 hrs, rinsed several times at room temperature and washed twice for 2 hrs at 50° C. in 1×SSC; 0.1% SDS. 12 genomic clones were identified; one was purified and analyzed by sequencing.

A DNA fragment corresponding to the hb DNA sequence was prepared by PCR from a mouse brain cDNA library and used as a probe to screen a mouse PCC4 teratocarcinoma cDNA library (Stratagene). One full-length cDNA clone, named mKsr-1, was obtained from 1×10$^6$ pfu screened. Using the mKsr-1 kinase domain as a probe, 1×10$^6$ pfu of a human fetal brain cDNA library (Clontech) was hybridized at reduced stringency (see above). Thirteen related cDNA clones were isolated and characterized by sequencing. They all represent partial transcripts and only one of them, named hKsr-1, has a complete kinase domain.

DNA sequences were performed by the dideoxy chain termination procedure (Sanger et al., 1977) using the Automated Laser Fluorescence (ALF) system (Pharmacia). Templates were prepared by sonicating plasmid DNA and inserting the sonicated DNA into the M13mp10 vector. The entire coding regions of βGGT-I and Ksr cDNAs from each species were sequenced on both strands as well as the genomic regions that correspond to the βGGT-1 and Dm ksr loci. Sequences were analysed using the Staden (R. Staden, MRC of Molecular Biology, Cambridge UK) and the Genetics Computer Group, Inc. software packages. The chromosomal regions for different βGGT-I and ksr mutant alleles were cloned into the λ_ZAP-express vector (Stratagene) and their respective coding regions were completely sequenced using oligonucleotide primers.

Cited References

Alexandropoulos, K., et al. (1995).Proc. Natl. Acad. Sci. USA 92, 3110–3114.

Altschul, S. F., et al. (1990) J. Mol. Biol. 215, 403–410.

Anderson, K. V. and Nüsslein-Volhard, C. (1984). Nature 311, 223–227.

Belvin, M. P., Jin, Y. and Anderson, K. V. (1995). Genes Dev. 9, 783–793.

Bier, E., et al. (1989). Genes Dev. 3, 1273–1287.

Bruder, J. T., Heidecker, B. and Rapp, U. R. (1992). Genes Dev. 6, 545–556.

Burgering, B. M. T. and Bos, J. L. (1995). Trends Biochem. Sci. 20, 18–22.

Buss, J. E., et al. (1989).Science 243, 1600–1603.

Cano, E. and Mahadevan, L. C. (1995). Trends Biochem. Sci. 20, 117–122.

Daum, G., et al. (1994). Trends Biochem. Sci. 19, 474–480.

Dent, P., et al. (1995). Science 268, 1902–1906.

Dent, P. and Sturgill, T. W. (1994). Proc. Natl. Acad. Sci. USA 91, 9544–9548.

Dickson, B., et al. (1992). Nature 360, 600–603.

Dougan, S. and DiNardo, S. (1992). Nature 360, 347–350.

Duffy, J. B. and Perrimon, N. (1994). Dev. Biol. 166, 380–395.

Fortini, M. E., Simon, M. A. and Rubin, G. M. (1992). Nature 355, 559–561.

Gatti, M. and Baker, B. S. (1989). Genes Dev. 3, 438–453.

Glomset, J. A. and Farnsworth, C. C. (1994). Annu. Rev. Cell Biol. 10, 181–205.

Hanks, S. K., Quinn, A. M. and Hunter, T. (1988). Science 241, 42–52.

Hardie, G. and Hanks, S. Eds. (1995). The protein kinase (part I): protein-serine kinases. (FactsBook Series, Academic Press inc.).

Heidecker, G., Kolch, W., Morrison, D. K. and Rapp, U. R. (1992). Adv. Can. Res. 58, 53–73.

Hou, X. S., Chou, T. B., Melnick, M. B. and Perrimon, N. (1995). Cell 81, 63–71.

Hubbard, S. R., et al. (1991). Science 254, 1776–1779.

Karpen, G. H. and Spradling, A. C. (1992). Genetics 132, 737–753.

Kato, K., et al. (1992). Proc. Natl. Acad. Sci.USA 89, 6403–6407.

Kimmel, B. E., Heberlein, U. and Rubin, G. M. (1990). Genes Dev. 4, 712–727.

Marshall, C. J. (1993). Science 259, 1865–1866.

Marshall, C. J. (1994). Curr. Opin. Genet. Dev. 4, 82–89.

McCormick, F. (1994a). Curr. Opin. Genet. Dev. 4, 71–76.

McCormick, F. (1994b).Trends Cell Biol. 4, 347–350.

Nassar, N., et al. (1995). Nature 375, 554–560.

Nehls, M., et al. (1994) (Genbank accession number X81634)

Sambrook, J., Fritsch, E. F. and Maniatis, T. (1989). Molecular Cloning: A Laboratory Manual, Second Edition (Cold Spring Harbor, New York: Cold Spring Harbor Laboratory Press).

Sanger, F., Nicklen, S. and Coulson, A. (1977). Proc. Natl. Acad. Sci. USA 74, 5463–5467.

Sidow, A. and Thomas, W. K. (1994) Curr. Biol. 4, 596–603.

Simon, M. A., et al. (1991). Cell 67, 701–716.

Simon, M. A., et al. (1985). Cell 42, 831–840.

Tamkun, J. W., et al. (1992). Cell 68, 561–572.

Tomlinson, A. and Ready, D. F. (1987). Dev. Biol. 123, 264–275.

van der Geer, P., et al. (1994). Annu. Rev. Cell Biol. 10, 251–337.

White, M. A., et al. (1995). Cell 80, 533–541.

Willumsen, B. M., et al. (1984). EMBO J. 3, 2581–2585.

Xu, T. and Rubin, G. M. (1993). Development 117, 1223–1237.

Pharmaceutical lead compound screening assays.

1. Protocol for Ksr—substrate phosphorylation assay.
   A. Reagents:
      Neutralite Avidin: 20 µg/ml in PBS.
      hKsr: $10^{-8}$–$10^{-5}$M hKsr at 20 µg/ml in PBS.
      Blocking Buffer: 5% BSA, 0.5% Tween 20 in PBS; 1 hour at room temperature.
      Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.
      -[$^{32}$P]γ-ATP 10×stock: $2\times10^{5}$M cold ATP with 100 µCi [$^{32}$P]γ-ATP. Place in the 4 °C. microfridge during screening.
      Substrate: $2\times10^{-6}$M biotinylated synthetic peptide kinase substrate (MBP, Sigma) at 20 µg/ml in PBS.
      Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
   B. Preparation of assay plates:
      Coat with 120 µl of stock Neutralite avidin per well overnight at 4° C.
      Wash 2 times with 200 µl PBS.
      Block with 150 µl of blocking buffer.
      Wash 2 times with 200 µl PBS.
   C. Assay:
      Add 40 µl assay buffer/well.
      Add 40 µl hKsr (0.1–10 pmoles/40 ul in assay buffer)
      Add 10 µl compound or extract.
      Shake at 30° C. for 15 minutes.
      Add 10 µl [$^{32}$P]γ-ATP 10×stock.
      Add 10 µl substrate.
      Shake at 30° C. for 15 minutes.
      Incubate additional 45 minutes at 30° C.
      Stop the reaction by washing 4 times with 200 µl PBS.
      Add 150 µl scintillation cocktail.
      Count in Topcount.
   D. Controls for all assays (located on each plate):
      a. Non-specific binding (no hKsr added)
      b. cold ATP to achieve 80% inhibition.

2. Protocol for hKsr—Raf binding assay.
   A. Reagents:
      Anti-myc antibody: 20 µg/ml in PBS.
      Blocking Buffer: 5% BSA, 0.5% Tween 20 in PBS; 1 hour at room temperature.
      Assay Buffer: 100 mM KCl, 20 mM HEPES pH 7.6, 0.25 mM EDTA, 1% glycerol, 0.5% NP-40, 50 mM β-mercaptoethanol, 1 mg/ml BSA, cocktail of protease inhibitors.
      $^{33}$P hKsr 10×stock: $10^{8}$–$10^{6}$M "cold" hKsr (full length) supplemented with 200,000–250,000 cpm of labeled hKsr (HMK-tagged) (Beckman counter). Place in the 4° C. microfridge during screening.
      Protease inhibitor cocktail (1000×): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma #S-6508) in 10 ml of PBS.
      Raf: $10^{-8}$–$10^{-5}$M myc eptitope-tagged Raf in PBS.
   B. Preparation of assay plates:
      Coat with 120 µl of stock anti-myc antibody per well overnight at 4° C.
      Wash 2× with 200 µl PBS.
      Block with 150 µl of blocking buffer.
      Wash 2× with 200 µl PBS.
   C. Assay:
      Add 40 µl assay buffer/well.
      Add 10 µl compound or extract.
      Add 10 µl $^{33}$P-hKsr (20,000–25,000 cpm/0.1–10 pmoles/well=$10^{-9}$–$10^{-7}$M final concentration).
      Shake at 25° C. for 15 minutes.
      Incubate additional 45 minutes at 25 °C.
      Add 40 µl eptitope-tagged Raf (0.1–10 pmoles/40 µl in assay buffer)
      Incubate 1 hour at room temperature.
      Stop the reaction by washing 4 times with 200 µl PBS.
      Add 150 µl scintillation cocktail.
      Count in Topcount.
   D. Controls for all assays (located on each plate):
      a. Non-specific binding (no hKsr added)
      b. Soluble (non-tagged Raf to achieve 80% inhibition.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

SEQUENCE LISTING

SEQ ID NO: 1 cDNA sequence of *Drosophila melanogaster* Ksr

SEQ ID NO: 2 amino acid sequence of *Drosophila melanogaster* Ksr

SEQ ID NO: 3 genomic sequence of *Drosophila virilis* Ksr 5,700,675

| 21 | 22 |

SEQ ID NO: 4 amino acid sequence of *Drosophila virilis* Ksr
SEQ ID NO: 5 cDNA sequence of Mus musculus Ksr
SEQ ID NO: 6 amino acid sequence of Mus musculus Ksr
SEQ ID NO: 7 cDNA composite sequence of human Ksr SEQ ID NO: 8 amino acid composite sequence of human Ksr
SEQ ID NO: 9 cDNA sequence of human Ksr'
SEQ ID NO: 10 amino acid sequence of human Ksr'

What is claimed is:

1. An isolated kinase suppressor of ras (Ksr) protein.

2. An isolated kinase suppressor of ras (Ksr) protein according to claim 1, wherein said protein is mammalian.

3. An isolated kinase suppressor of ras (Ksr) protein according to claim 1, wherein said protein is human.

4. A recombinant isolated Ksr protein produced by a cell comprising a nucleic acid encoding a kinase suppressor of ras (Ksr) according to claim 1 operably linked to a transcription regulatory region not naturally lined to a Ksr-encoding gene.

5. A recombinant isolated Ksr protein according to claim 4, wherein said cell is a mammalian cell, an avian cell, an insect cell, a fungal cell, an amphibian cell or a fish cell.

6. An isolated kinase suppressor of ras (Ksr) protein, wherein said protein is *D. melanogaster, D. virilis,* mouse or human.

7. A recombinant isolated Ksr protein produced by a cell comprising a nucleic acid encoding a kinase suppressor of ras (Ksr) according to claim 6 operably linked to a transcription regulatory region not naturally lined to a Ksr-encoding gene.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
      ( A ) LENGTH: 3697 base pairs
      ( B ) TYPE: nucleic acid
      ( C ) STRANDEDNESS: double
      ( D ) TOPOLOGY: linear ( i i ) MOLECULE TYPE: cDNA ( x i ) SEQUENCE DESCRIPTION: SEQ ID NO:1:

```
GAATTCCAAT TATTGCTTTT TCGCATTGCC TAAGCCGTTT AGAGTTGCGG GCGTTAGCGT       60
GCGCGATAGC CGGAGCACCG AACGTCAAGG TCGCTTGGCG AGGGCCACAA TGCGGGCGG       120
AGTCCCAGCC ATTGGTCCCA TCGAATCGTC GAGTCCCCGA GAGGCGTCT GAAAAAATCA      180
ATCGGGCTCC ACTCCGTCGC GAATAAGCAG GATGAGCAGC AACAACAACG CACCCGCATC      240
GGCTCCAGAC ACGGGCTCCA CCAATGCCAA CGATCCCATC TCCGGTTCGC TGTCCGTAGA      300
CAGCAACCTG GTTATCATTC AGGACATGAT TGATCTCTCG GCCAACCATC TGGAGGGCCT      360
GCGAACGCAG TGCGCGATCA GCTCCACGCT GACGCAGCAG GAGATTCGTT GCCTGGAGTC      420
GAAGCTGGTG CGATACTTCT CCGAGCTGCT GCTGGCGAAG ATGCGGCTAA ATGAGCGCAT      480
CCCGGCCAAC GGGCTTGTGC CCACACAAC GGGCAACGAA CTGAGGCAAT GGCTGCGCGT      540
AGTGGGCCTT AGCCAGGGGA CTCTTACCGC CTGCCTTGCT CGCCTGACCA CTCTAGAGCA      600
AAGCCTGCGT CTCAGCGACG AGGAGATCCG TCAACTCCTG GCTGACAGCC CAGCCAGCG      660
AGAGGAGGAG GAACTGCGAC GCCTGACCAG GGCCATGCAG AACTTAAGGA AGTGCATGGA      720
GTCGCTGGAG AGCGGTACTG CGGCTAGCAA CAACGATCCA GAGCAGTGGC ACTGGACTC      780
CTGGGACAGG CCCACCCACA TTCATCGCGG CAGTGTGGGA AACATTGGAC TGGGTAACAA      840
TTCAACCGCC TCCCGAGAA CCCATCATCG CCAGCATGGT GTCAAGGGAA AGAATTCCGC      900
TCTGGCCAAC TCCACCAACT TCAAAAGTGG CCGCCAATCG CCCTCAGCGA CAGAAGAGCT      960
GAACAGCACA CAGGGTTCCC AGCTGACTTT AACCCTTACG CCCTCGCCAC CCAATTCGCC     1020
CTTCACGCCT TCCAGTGGGC TGAGCAGCAG CCTTAATGGA ACACCACAGA GGAGTCGTGG     1080
TACCCCGCCG CCAGCCAGAA AGCACCAGAC CTTGCTGAGC CAGAGTCATG TGCAAGTGGA     1140
CGGGGAGCAA TTAGCCCGCA ACCGTTTGCC CACTGATCCC AGCCCCGATA GCCACAGCTC     1200
CACCAGCTCG GACATCTTTG TGGACCCAAA TACTAATGCC AGCTCCGGAG GAAGTTCCTC     1260
GAACGTGCTT ATGGTGCCAT GCTCTCCGGG CGTGGGTCAC GTGGGCATGG GTCATGCAAT     1320
CAAGCATCGT TTCACCAAGG CCCTGGGCTT CATGGCCACC TGTACCCTGT GCCAGAAGCA     1380
GGTCTTTCAC CGCTGGATGA AGTGCACCGA CTGCAAGTAC ATCTGCCACA AGTCATGCGC     1440
ACCGCACGTA CCGCCCTCCT GTGGACTTCC ACGAGAATAT GTGGACGAGT TCGGCACAT     1500
AAAGGAGCAG GGAGGATACG CCAGTCTGCC GCATGTGCAT GGCGCGGCGA AAGGATCCCC     1560
```

-continued

```
TTTGGTAAAA AAGAGCACCC TGGGTAAGCC CTTGCATCAG CAGCACGGCG ATAGCAGTTC    1620
GCCGAGTTCC AGCTGCACTA GTTCCACGCC CAGCAGTCCG GCGCTGTTCC AGCAAAGGGA    1680
GCGCGAGCTG GATCAGGCGG GCAGCAGCTC TAGCGCCAAT CTGTTACCTA CGCCTTCGCT    1740
TGGCAAGCAC CAGCCGAGTC AATTCAACTT TCCCAACGTG ACGGTGACGA GCAGTGGCGG    1800
AAGCGGTGGT GTATCGCTCA TCTCCAATGA ACCAGTGCCA GAGCAATTCC CCACGGCGCC    1860
TGCAACAGCC AACGGAGGAC TTGATAGTCT GGTGAGCAGC TCCAACGGGC ACATGAGCTC    1920
GCTCATCGGT AGCCAAACTT CAAACGCTTC TACTGCGGCC ACCTTGACGG GCAGTCTGGT    1980
CAATAGCACA ACCACCACCA GCACCTGCAG TTTCTTTCCG CGAAAATTGA GCACAGCCGG    2040
TGTGGATAAG AGGACGCCGT TCACCAGCGA GTGCACGGAT ACCCACAAGT CAAATGACAG    2100
CGACAAGACA GTCTCCTTGT CTGGAAGTGC CAGCACGGAC TCGGACCGGA CACCCGTTCG    2160
TGTGGATTCA ACGGAAGACG GAGACTCGGG ACAATGGCGA CAGAACTCGA TCTCACTCAA    2220
GGAATGGGAC ATCCCGTATG GTGATCTGCT TCTGCTCGAG CGGATAGGGC AGGGACGCTT    2280
CGGCACCGTG CATCGAGCCC TTTGGCACGG AGATGTGGCG GTTAAGCTGC TCAACGAGGA    2340
CTATCTGCAA GACGAACACA TGCTGGAGAC GTTTCGCAGC GAGGTAGCCA ACTTCAAGAA    2400
CACTCGACAC GAGAACCTGG TGCTGTTCAT GGGAGCCTGC ATGAACCCAC CATATTTGGC    2460
CATTGTGACT TCATTGTGCA AGGGCAACAC CTTGTATACG TATATTCACC AGCGTCGGGA    2520
GAAGTTTGCC ATGAACCGGA CTCTCCTCAT TGCCCAGCAG ATCGCCCAGG GCATGGGCTA    2580
CCTGCACGCA AGGGAGATCA TCCACAAAGA TCTGCGCACC AAGAACATCT TCATCGAGAA    2640
CGGCAAGGTG ATTATCACGG ACTTTGGGCT GTTCAGCTCC ACCAAGCTGC TCTACTGTGA    2700
TATGGGCCTA GGAGTGCCCC ACAACTGGTT GTGCTACCTG GCGCCGGAGC TAATCCGAGC    2760
ATTGCAGCCG GAGAAGCCGC GTGGAGAGTG TCTGGAGTTC ACCCCATACT CCGATGTCTA    2820
CTCTTTCGGA ACCGTTTGGT ACGAGCTAAT CTGCGGCGAG TTCACATTCA AGGATCAGCC    2880
GGCGGAATCG ATCATCTGGC AGGTTGGCCG TGGGATGAAG CAGTCGCTGG CCAACCTGCA    2940
GTCTGGACGG GATGTCAAGG ACTTGCTGAT GCTGTGCTGG ACCTACGAGA AGGAGCACCG    3000
GCCGCAGTTC GCACGCCTGC TCTCCCTGCT GGAGCATCTT CCCAAGAAGC GTCTGGCGCG    3060
CAGTCCCTCC CACCCCGTCA ACCTTTCCCG TTCCGCCGAG TCCGTGTTCT GAGGGAACTG    3120
CAGCATGGCC ACTGTCACTG TCTAGTACAA TTTCGATCTA CCAACTAAGC TAGCTCGCTT    3180
TGTGCCCTCG TCCACTCTAC ACAAACTCTC TCCCAAGGCG AAGTTCTATC GAGCCGAGCG    3240
AAGATTGTAA ATACATAAAC GTAACTACCA AATTATAGCA ATCCATTTTA AAAACTACAT    3300
ACATATGTGT AGGCATGTAT CGGGAGCACT CCAGTTGCAG TTGTTAGCAA ACGAAACAAA    3360
GGCAAATCAA ATGTTAACTC GAAAAGACA AAACGCTTAA ATGTTTAAGA GCAGAGGCAA     3420
ACAGAGAAGG CATAGACATA CATATACAAA CAAACAAACA AGCACTGTGG CAAACATAAA    3480
TGTAAACGTT AATCAGGTGA GCAATTTCTA AATTGTTAAT TATGTGTAAG AGAACTATAT    3540
ATATATATAT ATATATATAT ATATATATAT ATATACATGT ATATACAGCA GCAATGTATT    3600
GTATATGACG GACTAGTGTT AAATTAAATA TATATTGTGA ATTATGTATG GTCAAGTGTA    3660
TATAGTAAAT GGACTTTAAA TGCGAAATCG GGAATTC                             3697
```

( 2 ) INFORMATION FOR SEQ ID NO:2:

( i ) SEQUENCE CHARACTERISTICS:
        ( A ) LENGTH: 966 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:2:

```
Met Ser Ser Asn Asn Asn Ala Pro Ala Ser Ala Pro Asp Thr Gly Ser
 1               5                  10                  15
Thr Asn Ala Asn Asp Pro Ile Ser Gly Ser Leu Ser Val Asp Ser Asn
            20                  25                  30
Leu Val Ile Ile Gln Asp Met Ile Asp Leu Ser Ala Asn His Leu Glu
        35                  40                  45
Gly Leu Arg Thr Gln Cys Ala Ile Ser Ser Thr Leu Thr Gln Gln Glu
    50                  55                  60
Ile Arg Cys Leu Glu Ser Lys Leu Val Arg Tyr Phe Ser Glu Leu Leu
65                  70                  75                  80
Leu Ala Lys Met Arg Leu Asn Glu Arg Ile Pro Ala Asn Gly Leu Val
                85                  90                  95
Pro His Thr Thr Gly Asn Glu Leu Arg Gln Trp Leu Arg Val Val Gly
            100                 105                 110
Leu Ser Gln Gly Thr Leu Thr Ala Cys Leu Ala Arg Leu Thr Thr Leu
        115                 120                 125
Glu Gln Ser Leu Arg Leu Ser Asp Glu Glu Ile Arg Gln Leu Leu Ala
    130                 135                 140
Asp Ser Pro Ser Gln Arg Glu Glu Glu Glu Leu Arg Arg Leu Thr Arg
145                 150                 155                 160
Ala Met Gln Asn Leu Arg Lys Cys Met Glu Ser Leu Glu Ser Gly Thr
                165                 170                 175
Ala Ala Ser Asn Asn Asp Pro Glu Gln Trp His Trp Asp Ser Trp Asp
            180                 185                 190
Arg Pro Thr His Ile His Arg Gly Ser Val Gly Asn Ile Gly Leu Gly
        195                 200                 205
Asn Asn Ser Thr Ala Ser Pro Arg Thr His His Arg Gln His Gly Val
    210                 215                 220
Lys Gly Lys Asn Ser Ala Leu Ala Asn Ser Thr Asn Phe Lys Ser Gly
225                 230                 235                 240
Arg Gln Ser Pro Ser Ala Thr Glu Glu Leu Asn Ser Thr Gln Gly Ser
                245                 250                 255
Gln Leu Thr Leu Thr Leu Thr Pro Ser Pro Asn Ser Pro Phe Thr
            260                 265                 270
Pro Ser Ser Gly Leu Ser Ser Ser Leu Asn Gly Thr Pro Gln Arg Ser
        275                 280                 285
Arg Gly Thr Pro Pro Pro Ala Arg Lys His Gln Thr Leu Leu Ser Gln
    290                 295                 300
Ser His Val Gln Val Asp Gly Glu Gln Leu Ala Arg Asn Arg Leu Pro
305                 310                 315                 320
Thr Asp Pro Ser Thr Asp Ser His Ser Thr Ser Ser Asp Ile Phe
                325                 330                 335
Val Asp Pro Asn Thr Asn Ala Ser Ser Gly Gly Ser Ser Ser Asn Val
            340                 345                 350
Leu Met Val Pro Cys Ser Pro Gly Val Gly His Val Gly Met Gly His
        355                 360                 365
Ala Ile Lys His Arg Phe Thr Lys Ala Leu Gly Phe Met Ala Thr Cys
    370                 375                 380
Thr Leu Cys Gln Lys Gln Val Phe His Arg Trp Met Lys Cys Thr Asp
385                 390                 395                 400
```

-continued

```
Cys Lys Tyr Ile Cys His Lys Ser Cys Ala Pro His Val Pro Pro Ser
            405             410             415
Cys Gly Leu Pro Arg Glu Tyr Val Asp Glu Phe Arg His Ile Lys Glu
            420             425             430
Gln Gly Gly Tyr Ala Ser Leu Pro His Val His Gly Ala Ala Lys Gly
            435             440             445
Ser Pro Leu Val Lys Lys Ser Thr Leu Gly Lys Pro Leu His Gln Gln
            450             455             460
His Gly Asp Ser Ser Pro Ser Ser Ser Cys Thr Ser Ser Thr Pro
465             470             475             480
Ser Ser Pro Ala Leu Phe Gln Gln Arg Glu Arg Glu Leu Asp Gln Ala
            485             490             495
Gly Ser Ser Ser Ser Ala Asn Leu Leu Pro Thr Pro Ser Leu Gly Lys
            500             505             510
His Gln Pro Ser Gln Phe Asn Phe Pro Asn Val Thr Val Thr Ser Ser
            515             520             525
Gly Gly Ser Gly Gly Val Ser Leu Ile Ser Asn Glu Pro Val Pro Glu
            530             535             540
Gln Phe Pro Thr Ala Pro Ala Thr Ala Asn Gly Gly Leu Asp Ser Leu
545             550             555             560
Val Ser Ser Ser Asn Gly His Met Ser Ser Leu Ile Gly Ser Gln Thr
            565             570             575
Ser Asn Ala Ser Thr Ala Ala Thr Leu Thr Gly Ser Leu Val Asn Ser
            580             585             590
Thr Thr Thr Thr Ser Thr Cys Ser Phe Phe Pro Arg Lys Leu Ser Thr
            595             600             605
Ala Gly Val Asp Lys Arg Thr Pro Phe Thr Ser Glu Cys Thr Asp Thr
            610             615             620
His Lys Ser Asn Asp Ser Asp Lys Thr Val Ser Leu Ser Gly Ser Ala
625             630             635             640
Ser Thr Asp Ser Asp Arg Thr Pro Val Arg Val Asp Ser Thr Glu Asp
            645             650             655
Gly Asp Ser Gly Gln Trp Arg Gln Asn Ser Ile Ser Leu Lys Glu Trp
            660             665             670
Asp Ile Pro Tyr Gly Asp Leu Leu Leu Glu Arg Ile Gly Gln Gly
            675             680             685
Arg Phe Gly Thr Val His Arg Ala Leu Trp His Gly Asp Val Ala Val
            690             695             700
Lys Leu Leu Asn Glu Asp Tyr Leu Gln Asp Glu His Met Leu Glu Thr
705             710             715             720
Phe Arg Ser Glu Val Ala Asn Phe Lys Asn Thr Arg His Glu Asn Leu
            725             730             735
Val Leu Phe Met Gly Ala Cys Met Asn Pro Pro Tyr Leu Ala Ile Val
            740             745             750
Thr Ser Leu Cys Lys Gly Asn Thr Leu Tyr Thr Tyr Ile His Gln Arg
            755             760             765
Arg Glu Lys Phe Ala Met Asn Arg Thr Leu Leu Ile Ala Gln Gln Ile
            770             775             780
Ala Gln Gly Met Gly Tyr Leu His Ala Arg Glu Ile Ile His Lys Asp
785             790             795             800
Leu Arg Thr Lys Asn Ile Phe Ile Glu Asn Gly Lys Val Ile Ile Thr
            805             810             815
Asp Phe Gly Leu Phe Ser Ser Thr Lys Leu Leu Tyr Cys Asp Met Gly
            820             825             830
```

```
    Leu Gly Val Pro His Asn Trp Leu Cys Tyr Leu Ala Pro Glu Leu Ile
            835                 840                 845
    Arg Ala Leu Gln Pro Glu Lys Pro Arg Gly Glu Cys Leu Glu Phe Thr
        850                 855                 860
    Pro Tyr Ser Asp Val Tyr Ser Phe Gly Thr Val Trp Tyr Glu Leu Ile
    865                 870                 875                 880
    Cys Gly Glu Phe Thr Phe Lys Asp Gln Pro Ala Glu Ser Ile Ile Trp
                    885                 890                 895
    Gln Val Gly Arg Gly Met Lys Gln Ser Leu Ala Asn Leu Gln Ser Gly
                900                 905                 910
    Arg Asp Val Lys Asp Leu Leu Met Leu Cys Trp Thr Tyr Glu Lys Glu
            915                 920                 925
    His Arg Pro Gln Phe Ala Arg Leu Leu Ser Leu Leu Glu His Leu Pro
        930                 935                 940
    Lys Lys Arg Leu Ala Arg Ser Pro Ser His Pro Val Asn Leu Ser Arg
    945                 950                 955                 960
    Ser Ala Glu Ser Val Phe
                    965
```

( 2 ) INFORMATION FOR SEQ ID NO:3:

( i ) SEQUENCE CHARACTERISTICS:
        ( A ) LENGTH: 3681 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:3:

```
CCCCCAAAAA CTATAAAATT TTTCGCGTTT TTCTCATAGC AGAAGCTGTC TCGAAGTCCG      60
CATTTCGCAG GACTGTTCAT GTGTGCTTGC AGCAAGCGAA AAAAGCTGGT TGATGTGGAC    120
AGAATGTGTG TCAAAGTGGT GCAAACAACA AATGATTTGT AAGTGCGTCT GAAAAAATCA    180
ATCAGTTTGT ACTGCTGGAA GGGGCGGGCG GGCCACAACA AAATGAGCAG CAGCGCCGCC    240
GCCCAGCTGA CTGCGCCGCC AGTCAGCAAC AGCAACAGCA GCAGCAGTAA CAACAATACA    300
ACAACGACTG CGAGCGAAAG CAATCTAATC ATCATACAGG ATATGATTGA TCTCTCGGCC    360
AACCATCTGG AGGGTCTGCG AACACAGTGC GCAACGAGCG CGACGTTGAC GCAACAGGAG    420
ATCCGCTGCC TAGAGTCCAA GTTGGTGCGC TACTTCTCCG AACTGCTCTT GACCAAAACG    480
AGACTCAACG AACGCATACC CGCGAACGGT CTGCTGCCCC ATCATCAGGC TACCGGGAAC    540
GAGTTGCGCC AATGGCTGCG AGTAGTTGGA CTCAGTCCGG AGTCACTGAA TGCATGCCTA    600
GCGCGTCTAA CGACATTGGA GCAAACACTG CAGCTGAGCG ATGAAGAACT GAAACAACTG    660
CTTGCCCACA ATTCAAGTAC CCAGCTGGAC GAGGAACTGC GGCGGCTGAC CAAAGCGATG    720
CATAATCTCC GAAAATGCAT GGAAACGCTG GACAGCAGCG GCGCAGTTGC GTCCAACGTC    780
GATCCGGAAC AATGGCACTG GGACTCCTGG GATCGACCCC ATCCGCATCA CATGCACCGC    840
GGCAGCATTG GCAATATTGG CCTAGGACTA AGCAGCGCCT CACCTCGCGC CCATCATCGT    900
CAACATCAAC ATCAACACGC GAACAGCAAG CCGAAAATTG TTAACAATTC TGCCTCAAGC    960
TCCCGCAGCG AACAGCAACC ACTGACTGGT TCTCAGTTGA CCTTAACACT GACGCCCTCG   1020
CCACCCAACT CGCCCTTTAC GCCCGCCTCA GGGACGGCAT CCGCCAGCGG CACTCCGCAG   1080
CGCAGCCGCA GTACCACAAC AGCGGCGGGA ACGCCACCAC CAGCCAAGAA GCATCAAACG   1140
CTGCTCATGC ACAACAGCAG CGCTTCGGAA ACGGCACTCG CGGAGCAGCC TCCACGGCCA   1200
```

```
CCGCGCAGCC GTCTACCCAC AGATCCTAGC CCGGATAGCC ACAGCTCGGC CAGCAGTTCG   1260
GACATTTTTG TGGACGGTGG CAGTATCAAC AGCTCCAATG TACTACTAGT GCCGCCCTCG   1320
CCAGGTGTGG CACACGTGGG CATGGGTCAT ACCATTAAGC ACCGTTTCAG TAAATGGTTT   1380
GGCTTCATGG CCACGTGCAA ACTGTGCCAA AAGCAGATGA TGAGCCACTG GTTCAAGTGC   1440
ACCGACTGCA AATATATTTG CCACAAGTCC TGTGCGCCGC ATGTGCCGCC CTCGTGTGGC   1500
CTTCCACCCG AATATGTTCA CGAGTTTCGT CAAACTCAGG TGGGCGGCAG ATGGGACCCT   1560
GCGCAGCACA GCAGCAGCAA GGCATCACCA GTGCCCAGGA AGAGCACGCT GGGCAAACCG   1620
CAATTGCAGC AGCCACAGCT GCAGCACGGG GACAGCAGCT CACCAAGCTC GAGCTGCACC   1680
AGCTCAACGC CAGCAGTCC AGCATTGTTC AGCAGCAGC AACTGCAACT GGCCACGCCC   1740
AGCGCCTGCC AGCCGAAACC AGCACCAGCA GCGGTAGCAG CAGCAGCAAC ACAACAGGGT   1800
CAACAGAGTC AATTCAATTT CCCCAACGTG ACCATCACAA GCATCAATGC CTGCAATAGT   1860
AACGCCAGCG CTGCCCAAAC GCTCATATCC AATGAGCCGC AAGCGCATAT GGCCACAACG   1920
GAGTCCACGC TGACCAATGG CAACAACAAC AGCAGCTCCA ACAACGGGAG CAGCGCCAAC   1980
AACAATAGCA GCAGCAGCAG CAGCTGCTCC AATGGTCACC TGCACTCGCT GACTGGAAGT   2040
CAAGTGTCCA CGCATTCGGC TACCTCGCAA GTGTCGAATG TCAGTGGCAG CAGCTCGGCC   2100
ACCTACACCT CCAGTCTGGT GAACAGCGGC AGTTTCTTTC CGCGGAAATT GAGCAATGCT   2160
GGCGTGGACA AGCGGGTGCC CTTTACCAGC GAATATACGG ACACGCACAA GTCGAATGAT   2220
AGCGACAAGA CGGTTTCGTT GTCGGGCAGC GCCAGCACTG ACTCGGATCG CACGCCTGTG   2280
CGTTTGGACT CCACAGAGGA TGGCGACTCG GGCCAATGGC GGCAGAACTC CATATCATTG   2340
AAGGAATGGG ATATACCCTA TGGCGATTTG CACTTGCTGG AGCGCATTGG ACAGGGTCGA   2400
TTTGGCACCG TGCATCGGGC ACTGTGGCAT GGCGATGTCG CTGTGAAGCT GCTCAATGAA   2460
GACTATCTGC AGGACGAGCA CATGCTGGAA TCGTTTCGCA ACGAGGTGGC CAATTTCAAG   2520
AAGACGCGAC ACGAGAATCT GGTGCTGTTC ATGGGCGCCT GCATGAATCC GCCGTATTTG   2580
GCCATTGTCA CGGCACTATG CAAGGGCAAC ACCCTGTACA CCTATATACA TCAGCGAAGG   2640
GAGAAGTTTG CAATGAATCG CACGTTGTTG ATTGCCCAAC AGATTGCCCA GGGCATGGGC   2700
TATTTGCATG CCAGGGACAT AATACACAAG GATCTGCGCA CCAAGAACAT TTTTATAGAG   2760
AATGGCAAGG TGATCATTAC GGACTTTGGC CTATTCAGCT CCACAAAGCT GCTGTACTGT   2820
GATATGGGCT TGGGTGTTCC ACAAAACTGG CTCTGCTACC TGGCCCCGGA ACTAATACGC   2880
GCCCTGCAGC CGTGCAAGCC ACCCGGCGAG TGTCTAGAGT TCACGTCCTA CTCGGATGTT   2940
TACTCATTTG GCACCGTTTG GTACGAGCTA ATTTGCGGCG AATTCACGTT CAAGGATCAA   3000
CCGGCGGAGT CAATCATTTG GCAAGTGGGG CGCGGCATGA ACAGTCGCT GGCCAATCTG   3060
CAGTCTGGTC GTGATGTCAA GGACCTGCTG ATGCTGTGCT GGACCTATGA AAAGGAGCAC   3120
AGGCCGGACT TTGCACGTCT GCTCTCCTTG CTGGAGCATT TGCCAAAGAA GCGCCTGGCA   3180
CGCAGTCCCT CGCATCCTGT CAACCTCTCG CGCTCAGCGG AATCTGTATT CTAACCAGCC   3240
GATATACAAA TATATACGTT TATAGACAAA TATGTCATAT ATGTAAGCAG GCGCGCACAC   3300
ACTCACACAC ACACACACTC TATTTAGCAC AATTTCACGT TATATGTAAA TGTAAGCTAC   3360
ACACATATGC AAACATACGT ATGTCACTTT AACTGTAATT GTTGTGCGTG CAAAATGTCA   3420
AATGTGAAAT TAGCTCTCCG GTAAGGGAAG CAAGAGAATG CGGAGAGCAA AGCTCACTTC   3480
CTCAGCCTCA TGTATGTGTA TGTATGTGTA CGACCCTACG ACTCTCAAAG AAAAGTTCAA   3540
AGTGCATGTG TTACAAAACA AAAAACTGTA AATATACATT TAAAGCAAAT GAAACGAAAC   3600
```

```
TATACATATA TGTGTATATC CAATTATAGC AATTTACAAA TGCATTGTCA AAATAGTTTT        3660

TATCTTTAAT TATGTATTGA A                                                 3681
```

( 2 ) INFORMATION FOR SEQ ID NO:4:

( i ) SEQUENCE CHARACTERISTICS:
        ( A ) LENGTH: 1003 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:4:

```
Met Ser Ser Ser Ala Ala Ala Gln Leu Thr Ala Pro Pro Val Ser Asn
 1           5                  10                  15

Ser Asn Ser Ser Ser Ser Asn Asn Asn Thr Thr Thr Thr Ala Ser Glu
            20                  25                  30

Ser Asn Leu Ile Ile Ile Gln Asp Met Ile Asp Leu Ser Ala Asn His
            35                  40                  45

Leu Glu Gly Leu Arg Thr Gln Cys Ala Thr Ser Ala Thr Leu Thr Gln
 50                  55                  60

Gln Glu Ile Arg Cys Leu Glu Ser Lys Leu Val Arg Tyr Phe Ser Glu
 65                  70                  75                  80

Leu Leu Leu Thr Lys Thr Arg Leu Asn Glu Arg Ile Pro Ala Asn Gly
                 85                  90                  95

Leu Leu Pro His His Gln Ala Thr Gly Asn Glu Leu Arg Gln Trp Leu
            100                 105                 110

Arg Val Val Gly Leu Ser Pro Glu Ser Leu Asn Ala Cys Leu Ala Arg
            115                 120                 125

Leu Thr Thr Leu Glu Gln Thr Leu Gln Leu Ser Asp Glu Glu Leu Lys
130                 135                 140

Gln Leu Leu Ala His Asn Ser Ser Thr Gln Leu Asp Glu Glu Leu Arg
145                 150                 155                 160

Arg Leu Thr Lys Ala Met His Asn Leu Arg Lys Cys Met Glu Thr Leu
                165                 170                 175

Asp Ser Ser Gly Ala Val Ala Ser Asn Val Asp Pro Glu Gln Trp His
            180                 185                 190

Trp Asp Ser Trp Asp Arg Pro His Pro His His Met His Arg Gly Ser
            195                 200                 205

Ile Gly Asn Ile Gly Leu Gly Leu Ser Ser Ala Ser Pro Arg Ala His
            210                 215                 220

His Arg Gln His Gln His Gln His Ala Asn Ser Lys Pro Lys Ile Val
225                 230                 235                 240

Asn Asn Ser Ala Ser Ser Ser Arg Ser Glu Gln Pro Leu Thr Gly
            245                 250                 255

Ser Gln Leu Thr Leu Thr Leu Thr Pro Ser Pro Pro Asn Ser Pro Phe
            260                 265                 270

Thr Pro Ala Ser Gly Thr Ala Ser Ala Ser Gly Thr Pro Gln Arg Ser
            275                 280                 285

Arg Ser Thr Thr Thr Ala Ala Gly Thr Pro Pro Pro Ala Lys Lys His
    290                 295                 300

Gln Thr Leu Leu Met His Asn Ser Ser Ala Ser Glu Thr Ala Leu Ala
305                 310                 315                 320

Glu Gln Pro Pro Arg Pro Pro Arg Ser Arg Leu Pro Thr Asp Pro Ser
                325                 330                 335
```

```
Pro  Asp  Ser  His  Ser  Ser  Ala  Ser  Ser  Ser  Asp  Ile  Phe  Val  Asp  Gly
          340                      345                     350

Gly  Ser  Ile  Asn  Ser  Ser  Asn  Val  Leu  Leu  Val  Pro  Pro  Ser  Pro  Gly
          355                      360                     365

Val  Ala  His  Val  Gly  Met  Gly  His  Thr  Ile  Lys  His  Arg  Phe  Ser  Lys
          370                      375                     380

Trp  Phe  Gly  Phe  Met  Ala  Thr  Cys  Lys  Leu  Cys  Gln  Lys  Gln  Met  Met
385                      390                      395                     400

Ser  His  Trp  Phe  Lys  Cys  Thr  Asp  Cys  Lys  Tyr  Ile  Cys  His  Lys  Ser
               405                      410                     415

Cys  Ala  Pro  His  Val  Pro  Ser  Cys  Gly  Leu  Pro  Pro  Glu  Tyr  Val
          420                      425                     430

His  Glu  Phe  Arg  Gln  Thr  Gln  Val  Gly  Gly  Arg  Trp  Asp  Pro  Ala  Gln
          435                      440                     445

His  Ser  Ser  Ser  Lys  Ala  Ser  Pro  Val  Pro  Arg  Lys  Ser  Thr  Leu  Gly
     450                      455                      460

Lys  Pro  Gln  Leu  Gln  Gln  Pro  Gln  Leu  Gln  His  Gly  Asp  Ser  Ser  Ser
465                      470                      475                     480

Pro  Ser  Ser  Ser  Cys  Thr  Ser  Ser  Thr  Pro  Ser  Ser  Pro  Ala  Leu  Phe
               485                      490                     495

Gln  Gln  Gln  Gln  Leu  Gln  Leu  Ala  Thr  Pro  Ser  Ala  Cys  Gln  Pro  Lys
               500                      505                     510

Pro  Ala  Pro  Ala  Ala  Val  Ala  Ala  Ala  Ala  Thr  Gln  Gln  Gly  Gln  Gln
          515                      520                     525

Ser  Gln  Phe  Asn  Phe  Pro  Asn  Val  Thr  Ile  Thr  Ser  Ile  Asn  Ala  Cys
     530                      535                      540

Asn  Ser  Asn  Ala  Ser  Ala  Ala  Gln  Thr  Leu  Ile  Ser  Asn  Glu  Pro  Gln
545                      550                      555                     560

Ala  His  Met  Ala  Thr  Thr  Glu  Ser  Thr  Leu  Thr  Asn  Gly  Asn  Asn  Asn
               565                      570                     575

Ser  Ser  Ser  Asn  Asn  Gly  Ser  Ser  Ala  Asn  Asn  Ser  Ser  Ser  Ser
               580                      585                      590

Ser  Ser  Cys  Ser  Asn  Gly  His  Leu  His  Ser  Leu  Thr  Gly  Ser  Gln  Val
          595                      600                     605

Ser  Thr  His  Ser  Ala  Thr  Ser  Gln  Val  Ser  Asn  Val  Ser  Gly  Ser  Ser
     610                      615                      620

Ser  Ala  Thr  Tyr  Thr  Ser  Ser  Leu  Val  Asn  Ser  Gly  Ser  Phe  Phe  Pro
625                      630                      635                     640

Arg  Lys  Leu  Ser  Asn  Ala  Gly  Val  Asp  Lys  Arg  Val  Pro  Phe  Thr  Ser
               645                      650                     655

Glu  Tyr  Thr  Asp  Thr  His  Lys  Ser  Asn  Asp  Ser  Asp  Lys  Thr  Val  Ser
          660                      665                     670

Leu  Ser  Gly  Ser  Ala  Ser  Thr  Asp  Ser  Asp  Arg  Thr  Pro  Val  Arg  Leu
          675                      680                     685

Asp  Ser  Thr  Glu  Asp  Gly  Asp  Ser  Gly  Gln  Trp  Arg  Gln  Asn  Ser  Ile
     690                      695                      700

Ser  Leu  Lys  Glu  Trp  Asp  Ile  Pro  Tyr  Gly  Asp  Leu  His  Leu  Leu  Glu
705                      710                      715                     720

Arg  Ile  Gly  Gln  Gly  Arg  Phe  Gly  Thr  Val  His  Arg  Ala  Leu  Trp  His
                    725                      730                     735

Gly  Asp  Val  Ala  Val  Lys  Leu  Leu  Asn  Glu  Asp  Tyr  Leu  Gln  Asp  Glu
               740                      745                     750

His  Met  Leu  Glu  Ser  Phe  Arg  Asn  Glu  Val  Ala  Asn  Phe  Lys  Lys  Thr
```

-continued

|     |     |     |     |     | 755 |     |     |     |     | 760 |     |     |     |     | 765 |
| --- | --- | --- | --- | --- | --- | --- | --- | --- | --- | --- | --- | --- | --- | --- | --- |
| Arg | His | Glu | Asn | Leu | Val | Leu | Phe | Met | Gly | Ala | Cys | Met | Asn | Pro | Pro |
|     | 770 |     |     |     |     | 775 |     |     |     |     | 780 |     |     |     |     |
| Tyr | Leu | Ala | Ile | Val | Thr | Ala | Leu | Cys | Lys | Gly | Asn | Thr | Leu | Tyr | Thr |
| 785 |     |     |     |     | 790 |     |     |     |     | 795 |     |     |     |     | 800 |
| Tyr | Ile | His | Gln | Arg | Arg | Glu | Lys | Phe | Ala | Met | Asn | Arg | Thr | Leu | Leu |
|     |     |     |     | 805 |     |     |     |     | 810 |     |     |     |     | 815 |     |
| Ile | Ala | Gln | Gln | Ile | Ala | Gln | Gly | Met | Gly | Tyr | Leu | His | Ala | Arg | Asp |
|     |     |     | 820 |     |     |     |     | 825 |     |     |     |     | 830 |     |     |
| Ile | Ile | His | Lys | Asp | Leu | Arg | Thr | Lys | Asn | Ile | Phe | Ile | Glu | Asn | Gly |
|     |     | 835 |     |     |     |     | 840 |     |     |     |     | 845 |     |     |     |
| Lys | Val | Ile | Ile | Thr | Asp | Phe | Gly | Leu | Phe | Ser | Ser | Thr | Lys | Leu | Leu |
|     | 850 |     |     |     |     | 855 |     |     |     |     | 860 |     |     |     |     |
| Tyr | Cys | Asp | Met | Gly | Leu | Gly | Val | Pro | Gln | Asn | Trp | Leu | Cys | Tyr | Leu |
| 865 |     |     |     |     | 870 |     |     |     |     | 875 |     |     |     |     | 880 |
| Ala | Pro | Glu | Leu | Ile | Arg | Ala | Leu | Gln | Pro | Cys | Lys | Pro | Pro | Gly | Glu |
|     |     |     |     | 885 |     |     |     |     | 890 |     |     |     |     | 895 |     |
| Cys | Leu | Glu | Phe | Thr | Ser | Tyr | Ser | Asp | Val | Tyr | Ser | Phe | Gly | Thr | Val |
|     |     |     | 900 |     |     |     |     | 905 |     |     |     |     | 910 |     |     |
| Trp | Tyr | Glu | Leu | Ile | Cys | Gly | Glu | Phe | Thr | Phe | Lys | Asp | Gln | Pro | Ala |
|     |     | 915 |     |     |     |     | 920 |     |     |     |     | 925 |     |     |     |
| Glu | Ser | Ile | Ile | Trp | Gln | Val | Gly | Arg | Gly | Met | Lys | Gln | Ser | Leu | Ala |
|     | 930 |     |     |     |     | 935 |     |     |     |     | 940 |     |     |     |     |
| Asn | Leu | Gln | Ser | Gly | Arg | Asp | Val | Lys | Asp | Leu | Leu | Met | Leu | Cys | Trp |
| 945 |     |     |     |     | 950 |     |     |     |     | 955 |     |     |     |     | 960 |
| Thr | Tyr | Glu | Lys | Glu | His | Arg | Pro | Asp | Phe | Ala | Arg | Leu | Leu | Ser | Leu |
|     |     |     |     | 965 |     |     |     |     | 970 |     |     |     |     | 975 |     |
| Leu | Glu | His | Leu | Pro | Lys | Lys | Arg | Leu | Ala | Arg | Ser | Pro | Ser | His | Pro |
|     |     |     | 980 |     |     |     |     | 985 |     |     |     |     | 990 |     |     |
| Val | Asn | Leu | Ser | Arg | Ser | Ala | Glu | Ser | Val | Phe |     |     |     |     |     |
|     |     |     | 995 |     |     |     |     | 1000 |     |     |     |     |     |     |     |

( 2 ) INFORMATION FOR SEQ ID NO:5:

( i ) SEQUENCE CHARACTERISTICS:
       ( A ) LENGTH: 4094 base pairs
       ( B ) TYPE: nucleic acid
       ( C ) STRANDEDNESS: double
       ( D ) TOPOLOGY: linear ( i i ) MOLECULE TYPE: cDNA ( x i ) SEQUENCE DESCRIPTION: SEQ ID NO:5:

| GAATTCCCTC | GGGGCTTTCC | TGCCGAGGCG | CCCGTGTCCC | CGGGCTCCTC | GCCTCGGCCC | 60 |
| --- | --- | --- | --- | --- | --- | --- |
| CCAGCGGCCC | CGATGCCGAG | GCATGGATAG | AGCGGCGTTG | CGCGCGGCAG | CGATGGGCGA | 120 |
| GAAAAGGAG | GGCGGCGGCG | GGGCGCCGC | GGCGGACGGG | GGCGCAGGGG | CCGCCGTCAG | 180 |
| CCGGGCGCTG | CAGCAGTGCG | GCCAGCTGCA | GAAGCTCATC | GATATCTCCA | TCGGCAGTCT | 240 |
| GCGCGGGCTG | CGCACCAAGT | GCTCAGTGTC | TAACGACCTC | ACACAGCAGG | AGATCCGGAC | 300 |
| CCTAGAGGCA | AAGCTGGTGA | AATACATTTG | CAAGCAGCAG | CAGAGCAAGC | TTAGTGTGAC | 360 |
| CCCAAGCGAC | AGGACCGCCG | AGCTCAACAG | CTACCCACGC | TTCAGTGACT | GGCTGTACAT | 420 |
| CTTCAACGTG | AGGCCTGAGG | TGGTGCAGGA | GATCCCCCAA | GAGCTCACAC | TGGATGCTCT | 480 |
| GCTGGAGATG | GACGAGGCCA | AAGCCAAGGA | GATGCTGCGG | CGCTGGGGGG | CCAGCACGGA | 540 |
| GGAGTGCAGC | CGCCTACAGC | AAGCCCTTAC | CTGCCTTCGG | AAGGTGACTG | GCCTGGGAGG | 600 |

-continued

| | | | | | |
|---|---|---|---|---|---|
| GGAGCACAAA | ATGGACTCAG | GTTGGAGTTC | AACAGATGCT | CGAGACAGTA | GCTTGGGGCC | 660 |
| TCCCATGGAC | ATGCTTTCCT | CGCTGGGCAG | AGCGGGTGCC | AGCACTCAGG | GACCCCGTTC | 720 |
| CATCTCCGTG | TCCGCCCTGC | CTGCCTCAGA | CTCTCCGGTC | CCCGGCCTCA | GTGAGGGCCT | 780 |
| CTCGGACTCC | TGTATCCCCT | TGCACACCAG | CGGCCGGCTG | ACCCCCGGG | CCCTGCACAG | 840 |
| CTTCATCACG | CCCCCTACCA | CACCCCAGCT | ACGACGGCAC | GCCAAGCTGA | AGCCACCAAG | 900 |
| GACACCCCCA | CCGCCAAGCC | GCAAGGTCTT | CCAGCTGCTC | CCCAGCTTCC | CCACACTCAC | 960 |
| ACGGAGCAAG | TCCCACGAGT | CCCAGCTGGG | AAACCGAATC | GACGACGTCA | CCCCGATGAA | 1020 |
| GTTTGAACTC | CCTCATGGAT | CCCCACAGCT | GGTACGAAGG | GATATCGGGC | TCTCGGTGAC | 1080 |
| GCACAGGTTC | TCCACAAAGT | CATGGTTGTC | ACAGGTGTGC | AACGTGTGCC | AGAAGAGCAT | 1140 |
| GATTTTTGGC | GTGAAGTGCA | AACACTGCAG | GTTAAAATGC | CATAACAAGT | GCACAAAGGA | 1200 |
| AGCTCCCGCC | TGCAGGATCA | CCTTCCTCCC | ACTGGCCAGG | CTTCGGAGGA | CAGAGTCTGT | 1260 |
| CCCGTCAGAT | ATCAACAACC | CAGTGGACAG | AGCAGCAGAG | CCCCATTTTG | GAACCCTTCC | 1320 |
| CAAGGCCCTG | ACAAAGAAGG | AGCACCCTCC | AGCCATGAAC | CTGGACTCCA | GCAGCAACCC | 1380 |
| ATCCTCCACC | ACGTCCTCCA | CACCCTCATC | GCCGGCACCT | TTCCTGACCT | CATCTAATCC | 1440 |
| CTCCAGTGCC | ACCACGCCTC | CCAACCCGTC | ACCTGGCCAG | CGGGACAGCA | GGTTCAGCTT | 1500 |
| CCCAGACATT | TCAGCCTGTT | CTCAGGCAGC | CCCGCTGTCC | AGCACAGCCG | ACAGTACACG | 1560 |
| GCTCGACGAC | CAGCCCAAAA | CAGATGTGCT | AGGTGTTCAC | GAAGCAGAGG | CTGAGGAGCC | 1620 |
| TGAGGCTGGC | AAGTCAGAGG | CAGAGGATGA | CGAGGAGGAT | GAGGTGGACG | ACCTCCCCAG | 1680 |
| CTCCCGCCGG | CCCTGGAGGG | GCCCCATCTC | TCGAAAGGCC | AGCCAGACCA | GCGTTTACCT | 1740 |
| GCAAGAGTGG | GACATCCCCT | TTGAACAGGT | GGAACTGGGC | GAGCCCATTG | ACAGGGTCG | 1800 |
| CTGGGGCCGG | GTGCACCGAG | GCCGTTGGCA | TGGCGAGGTG | GCCATTCGGC | TGCTGGAGAT | 1860 |
| GGACGGCCAC | AATCAGGACC | ACCTGAAGCT | GTTCAAGAAA | GAGGTGATGA | ACTACCGGCA | 1920 |
| GACGCGGCAT | GAGAACGTGG | TGCTCTTCAT | GGGGGCCTGC | ATGAACCCAC | CTCACCTGGC | 1980 |
| CATTATCACC | AGCTTCTGCA | AGGGGCGGAC | ATTGCATTCA | TTCGTGAGGG | ACCCCAAGAC | 2040 |
| GTCTCTGGAC | ATCAATAAGA | CTAGGCAGAT | CGCCCAGGAG | ATCATCAAGG | GCATGGGTTA | 2100 |
| TCTTCATGCA | AAAGGCATCG | TGCACAAGGA | CCTCAAGTCC | AAGAATGTCT | TCTATGACAA | 2160 |
| CGGCAAAGTG | GTCATCACAG | ACTTCGGGCT | GTTTGGATC | TCGGGTGTGG | TCCGAGAGGA | 2220 |
| ACGGCGCGAG | AACCAACTGA | AACTGTCACA | TGACTGGCTG | TGCTACCTGG | CCCCCGAGAT | 2280 |
| CGTACGAGAA | ATGATCCCGG | GCGGGACGA | GGACCAGCTG | CCCTTCTCCA | AAGCAGCCGA | 2340 |
| TGTCTATGCA | TTCGGGACTG | TGTGGTATGA | ACTACAGGCA | AGAGACTGGC | CCTTTAAGCA | 2400 |
| CCAGCCTGCT | GAGGCCTTGA | TCTGGCAGAT | TGGAAGTGGG | GAAGGAGTAC | GGCGCGTCCT | 2460 |
| GGCATCCGTC | AGCCTGGGGA | AGGAAGTCGG | CGAGATCCTG | TCTGCCTGCT | GGGCTTTCGA | 2520 |
| TCTGCAGGAG | AGACCCAGCT | TCAGCCTGCT | GATGGACATG | CTGGAGAGGC | TGCCCAAGCT | 2580 |
| GAACCGGCGG | CTCTCCCACC | CTGGGCACTT | TTGGAAGTCG | GCTGACATTA | ACAGCAGCAA | 2640 |
| AGTCATGCCC | CGCTTTGAAA | GGTTTGGCCT | GGGGACCCTG | GAGTCCGGTA | ATCCAAAGAT | 2700 |
| GTAGCCAGCC | CTGCACGTTC | ATGCAGAGAG | TGTCTTCCTT | TCGAAAACAT | GATCACGAAA | 2760 |
| CATGCAGACC | ACCACCTCAA | GGAATCAGAA | GCATTGCATC | CCAAGCTGCG | GACTGGGAGC | 2820 |
| GTGTCTCCTC | CCTAAAGGAC | GTGCGTGCGT | GCGTGCGTGC | GTGCGTGCGT | GCGTGCGTCA | 2880 |
| CCAAGGTGTG | TGGAGCTCAG | GATCGCAGCC | ATACACGCAA | CTCCAGATGA | TACCACTACC | 2940 |
| GCCAGTGTTT | ACACAGAGGT | TTCTGCCTGG | CAAGCTTGGT | ATTTTACAGT | AGGTGAAGAT | 3000 |

-continued

| | | | | | |
|---|---|---|---|---|---|
| CATTCTGCAG | AAGGGTGCTG | GCACAGTGGA | GCAGCACGGA | TGTCCCCAGC | CCCCGTTCTG | 3060 |
| GAAGACCCTA | CAGCTGTGAG | AGGCCCAGGG | TTGAGCCAGA | TGAAAGAAAA | GCTGCGTGGG | 3120 |
| TGTGGGCTGT | ACCCGGAAAA | GGGCAGGTGG | CAGGAGGTTT | GCCTTGGCCT | GTGCTTGGGC | 3180 |
| CGAGAACCAC | ACTAAGGAGC | AGCAGCCTGA | GTTAGGAATC | TATCTGGATT | ACGGGGATCA | 3240 |
| GAGTTCCTGG | AGAGTGGACT | CAGTTTCTGC | TCTGATCCAG | GCCTGTTGTG | CTTTTTTTT | 3300 |
| TTCCCCCTTA | AAAAAAAAA | AGTACAGACA | GAATCTCAGC | GGCTTCTAGA | CTGATCTGAT | 3360 |
| GGATCTTAGC | CCGGCTTCTA | CTGCGGGGGG | GAGGGGGGGA | GGGATAGCCA | CATATCTGTG | 3420 |
| GAGACACCCA | CTTCTTTATC | TGAGGCCTCC | AGGTAGGCAC | AAAGGCTGTG | GAACTCAGCC | 3480 |
| TCTATCATCA | GACACCCCCC | CCCAATGCCT | CATTGACCCC | CTTCCCCCAG | AGCCAAGGGC | 3540 |
| TAGCCCATCG | GGTGTGTGTA | CAGTAAGTTC | TTGGTGAAGG | AGAACAGGGA | CGTTGGCAGA | 3600 |
| AGCAGTTTGC | AGTGGCCCTA | GCATCTTAAA | ACCCATTGTC | TGTCACACCA | GAAGGTTCTA | 3660 |
| GACCTACCAC | CACTTCCCTT | CCCCATCTCA | TGGAAACCTT | TTAGCCCATT | CTGACCCCTG | 3720 |
| TGTGTGCTCT | GAGCTCAGAT | CGGGTTATGA | GACCGCCCAG | GCACATCAGT | CAGGGAGGCT | 3780 |
| CTGATGTGAG | CCGCAGACCT | CTGTGTTCAT | TCCTATGAGC | TGGAGGGGCT | GGACTGGGTG | 3840 |
| GGGTCAGATG | TGCTTGGCAG | GAACTGTCAG | CTGCTGAGCA | GGGTGGTCCC | TGAGCGGAGG | 3900 |
| ATAAGCAGCA | TCAGACTCCA | CAACCAGAGG | AAGAAAGAAA | TGGGGATGGA | GCGGAGACCC | 3960 |
| ACGGGCTGAG | TCCCGCTGTG | GAGTGGCCTT | GCAGCTCCCT | CTCAGTTAAA | ACTCCCAGTA | 4020 |
| AAGCCACAGT | TCTCCGAGCA | CCCAAGTCTG | CTCCAGCCGT | CTCTTAAAAC | AGGCCACTCT | 4080 |
| CTGAGAAGGA | ATTC | | | | | 4094 |

( 2 ) INFORMATION FOR SEQ ID NO:6:

( i ) SEQUENCE CHARACTERISTICS:
( A ) LENGTH: 873 amino acids
( B ) TYPE: amino acid
( C ) STRANDEDNESS: Not Relevant
( D ) TOPOLOGY: Not Relevant ( i i ) MOLECULE TYPE: peptide ( x i ) SEQUENCE DESCRIPTION: SEQ ID NO:6:

| Met | Asp | Arg | Ala | Ala | Leu | Arg | Ala | Ala | Ala | Met | Gly | Glu | Lys | Lys | Glu |
|---|---|---|---|---|---|---|---|---|---|---|---|---|---|---|---|
| 1 | | | | 5 | | | | | 10 | | | | | 15 | |

| Gly | Gly | Gly | Gly | Gly | Ala | Ala | Ala | Asp | Gly | Gly | Ala | Gly | Ala | Ala | Val |
|---|---|---|---|---|---|---|---|---|---|---|---|---|---|---|---|
| | | | 20 | | | | | 25 | | | | | 30 | | |

| Ser | Arg | Ala | Leu | Gln | Gln | Cys | Gly | Gln | Leu | Gln | Lys | Leu | Ile | Asp | Ile |
|---|---|---|---|---|---|---|---|---|---|---|---|---|---|---|---|
| | | | 35 | | | | 40 | | | | | 45 | | | |

| Ser | Ile | Gly | Ser | Leu | Arg | Gly | Leu | Arg | Thr | Lys | Cys | Ser | Val | Ser | Asn |
|---|---|---|---|---|---|---|---|---|---|---|---|---|---|---|---|
| | 50 | | | | | 55 | | | | | 60 | | | | |

| Asp | Leu | Thr | Gln | Gln | Glu | Ile | Arg | Thr | Leu | Glu | Ala | Lys | Leu | Val | Lys |
|---|---|---|---|---|---|---|---|---|---|---|---|---|---|---|---|
| 65 | | | | | 70 | | | | | 75 | | | | | 80 |

| Tyr | Ile | Cys | Lys | Gln | Gln | Gln | Ser | Lys | Leu | Ser | Val | Thr | Pro | Ser | Asp |
|---|---|---|---|---|---|---|---|---|---|---|---|---|---|---|---|
| | | | | 85 | | | | | 90 | | | | | 95 | |

| Arg | Thr | Ala | Glu | Leu | Asn | Ser | Tyr | Pro | Arg | Phe | Ser | Asp | Trp | Leu | Tyr |
|---|---|---|---|---|---|---|---|---|---|---|---|---|---|---|---|
| | | | | 100 | | | | 105 | | | | | 110 | | |

| Ile | Phe | Asn | Val | Arg | Pro | Glu | Val | Val | Gln | Glu | Ile | Pro | Gln | Glu | Leu |
|---|---|---|---|---|---|---|---|---|---|---|---|---|---|---|---|
| | | | 115 | | | | 120 | | | | | 125 | | | |

| Thr | Leu | Asp | Ala | Leu | Leu | Glu | Met | Asp | Glu | Ala | Lys | Ala | Lys | Glu | Met |
|---|---|---|---|---|---|---|---|---|---|---|---|---|---|---|---|
| | | 130 | | | | | 135 | | | | | 140 | | | |

| Leu | Arg | Arg | Trp | Gly | Ala | Ser | Thr | Glu | Glu | Cys | Ser | Arg | Leu | Gln | Gln |
|---|---|---|---|---|---|---|---|---|---|---|---|---|---|---|---|
| 145 | | | | | 150 | | | | | 155 | | | | | 160 |

-continued

```
Ala  Leu  Thr  Cys  Leu  Arg  Lys  Val  Thr  Gly  Leu  Gly  Gly  Glu  His  Lys
               165                      170                     175

Met  Asp  Ser  Gly  Trp  Ser  Ser  Thr  Asp  Ala  Arg  Asp  Ser  Ser  Leu  Gly
               180                      185                     190

Pro  Pro  Met  Asp  Met  Leu  Ser  Ser  Leu  Gly  Arg  Ala  Gly  Ala  Ser  Thr
               195                      200                     205

Gln  Gly  Pro  Arg  Ser  Ile  Ser  Val  Ser  Ala  Leu  Pro  Ala  Ser  Asp  Ser
               210                      215                     220

Pro  Val  Pro  Gly  Leu  Ser  Glu  Gly  Leu  Ser  Asp  Ser  Cys  Ile  Pro  Leu
225                      230                     235                     240

His  Thr  Ser  Gly  Arg  Leu  Thr  Pro  Arg  Ala  Leu  His  Ser  Phe  Ile  Thr
               245                      250                     255

Pro  Pro  Thr  Thr  Pro  Gln  Leu  Arg  Arg  His  Ala  Lys  Leu  Lys  Pro  Pro
               260                      265                     270

Arg  Thr  Pro  Pro  Pro  Ser  Arg  Lys  Val  Phe  Gln  Leu  Leu  Pro  Ser
               275                      280                     285

Phe  Pro  Thr  Leu  Thr  Arg  Ser  Lys  Ser  His  Glu  Ser  Gln  Leu  Gly  Asn
     290                      295                     300

Arg  Ile  Asp  Asp  Val  Thr  Pro  Met  Lys  Phe  Glu  Leu  Pro  His  Gly  Ser
305                      310                     315                     320

Pro  Gln  Leu  Val  Arg  Arg  Asp  Ile  Gly  Leu  Ser  Val  Thr  His  Arg  Phe
               325                      330                     335

Ser  Thr  Lys  Ser  Trp  Leu  Ser  Gln  Val  Cys  Asn  Val  Cys  Gln  Lys  Ser
               340                      345                     350

Met  Ile  Phe  Gly  Val  Lys  Cys  Lys  His  Cys  Arg  Leu  Lys  Cys  His  Asn
               355                      360                     365

Lys  Cys  Thr  Lys  Glu  Ala  Pro  Ala  Cys  Arg  Ile  Thr  Phe  Leu  Pro  Leu
     370                      375                     380

Ala  Arg  Leu  Arg  Arg  Thr  Glu  Ser  Val  Pro  Ser  Asp  Ile  Asn  Asn  Pro
385                      390                     395                     400

Val  Asp  Arg  Ala  Ala  Glu  Pro  His  Phe  Gly  Thr  Leu  Pro  Lys  Ala  Leu
               405                      410                     415

Thr  Lys  Lys  Glu  His  Pro  Pro  Ala  Met  Asn  Leu  Asp  Ser  Ser  Ser  Asn
               420                      425                     430

Pro  Ser  Ser  Thr  Thr  Ser  Ser  Thr  Pro  Ser  Ser  Pro  Ala  Pro  Phe  Leu
               435                      440                     445

Thr  Ser  Ser  Asn  Pro  Ser  Ser  Ala  Thr  Thr  Pro  Pro  Asn  Pro  Ser  Pro
     450                      455                     460

Gly  Gln  Arg  Asp  Ser  Arg  Phe  Ser  Phe  Pro  Asp  Ile  Ser  Ala  Cys  Ser
465                      470                     475                     480

Gln  Ala  Ala  Pro  Leu  Ser  Ser  Thr  Ala  Asp  Ser  Thr  Arg  Leu  Asp  Asp
               485                      490                     495

Gln  Pro  Lys  Thr  Asp  Val  Leu  Gly  Val  His  Glu  Ala  Glu  Ala  Glu  Glu
               500                      505                     510

Pro  Glu  Ala  Gly  Lys  Ser  Glu  Ala  Glu  Asp  Asp  Glu  Asp  Glu  Val
               515                      520                     525

Asp  Asp  Leu  Pro  Ser  Ser  Arg  Arg  Pro  Trp  Arg  Gly  Pro  Ile  Ser  Arg
530                      535                     540

Lys  Ala  Ser  Gln  Thr  Ser  Val  Tyr  Leu  Gln  Glu  Trp  Asp  Ile  Pro  Phe
545                      550                     555                     560

Glu  Gln  Val  Glu  Leu  Gly  Glu  Pro  Ile  Gly  Gln  Gly  Arg  Trp  Gly  Arg
               565                      570                     575

Val  His  Arg  Gly  Arg  Trp  His  Gly  Glu  Val  Ala  Ile  Arg  Leu  Leu  Glu
```

|       |       |       |       |       |       |       |       |       |       |       |       |       |       |       |
|-------|-------|-------|-------|-------|-------|-------|-------|-------|-------|-------|-------|-------|-------|-------|
|       |       |       |       | 580   |       |       |       |       | 585   |       |       |       |       | 590   |
| Met   | Asp   | Gly   | His   | Asn   | Gln   | Asp   | His   | Leu   | Lys   | Leu   | Phe   | Lys   | Lys   | Glu   | Val |
|       |       | 595   |       |       |       |       | 600   |       |       |       |       | 605   |       |       |
| Met   | Asn   | Tyr   | Arg   | Gln   | Thr   | Arg   | His   | Glu   | Asn   | Val   | Val   | Leu   | Phe   | Met   | Gly |
|       |       | 610   |       |       |       | 615   |       |       |       |       | 620   |       |       |       |
| Ala   | Cys   | Met   | Asn   | Pro   | Pro   | His   | Leu   | Ala   | Ile   | Ile   | Thr   | Ser   | Phe   | Cys   | Lys |
| 625   |       |       |       |       | 630   |       |       |       |       | 635   |       |       |       |       | 640 |
| Gly   | Arg   | Thr   | Leu   | His   | Ser   | Phe   | Val   | Arg   | Asp   | Pro   | Lys   | Thr   | Ser   | Leu   | Asp |
|       |       |       |       | 645   |       |       |       |       | 650   |       |       |       |       | 655   |
| Ile   | Asn   | Lys   | Thr   | Arg   | Gln   | Ile   | Ala   | Gln   | Glu   | Ile   | Ile   | Lys   | Gly   | Met   | Gly |
|       |       |       | 660   |       |       |       |       | 665   |       |       |       |       | 670   |       |
| Tyr   | Leu   | His   | Ala   | Lys   | Gly   | Ile   | Val   | His   | Lys   | Asp   | Leu   | Lys   | Ser   | Lys   | Asn |
|       |       | 675   |       |       |       |       | 680   |       |       |       |       | 685   |       |       |
| Val   | Phe   | Tyr   | Asp   | Asn   | Gly   | Lys   | Val   | Val   | Ile   | Thr   | Asp   | Phe   | Gly   | Leu   | Phe |
|       | 690   |       |       |       |       | 695   |       |       |       | 700   |       |       |       |       |
| Gly   | Ile   | Ser   | Gly   | Val   | Val   | Arg   | Glu   | Glu   | Arg   | Arg   | Glu   | Asn   | Gln   | Leu   | Lys |
| 705   |       |       |       |       | 710   |       |       |       | 715   |       |       |       |       |       | 720 |
| Leu   | Ser   | His   | Asp   | Trp   | Leu   | Cys   | Tyr   | Leu   | Ala   | Pro   | Glu   | Ile   | Val   | Arg   | Glu |
|       |       |       |       | 725   |       |       |       |       | 730   |       |       |       |       | 735   |
| Met   | Ile   | Pro   | Gly   | Arg   | Asp   | Glu   | Asp   | Gln   | Leu   | Pro   | Phe   | Ser   | Lys   | Ala   | Ala |
|       |       |       | 740   |       |       |       |       | 745   |       |       |       |       | 750   |       |
| Asp   | Val   | Tyr   | Ala   | Phe   | Gly   | Thr   | Val   | Trp   | Tyr   | Glu   | Leu   | Gln   | Ala   | Arg   | Asp |
|       |       | 755   |       |       |       |       | 760   |       |       |       |       | 765   |       |       |
| Trp   | Pro   | Phe   | Lys   | His   | Gln   | Pro   | Ala   | Glu   | Ala   | Leu   | Ile   | Trp   | Gln   | Ile   | Gly |
|       | 770   |       |       |       |       | 775   |       |       |       |       | 780   |       |       |       |
| Ser   | Gly   | Glu   | Gly   | Val   | Arg   | Arg   | Val   | Leu   | Ala   | Ser   | Val   | Ser   | Leu   | Gly   | Lys |
| 785   |       |       |       |       | 790   |       |       |       |       | 795   |       |       |       |       | 800 |
| Glu   | Val   | Gly   | Glu   | Ile   | Leu   | Ser   | Ala   | Cys   | Trp   | Ala   | Phe   | Asp   | Leu   | Gln   | Glu |
|       |       |       |       | 805   |       |       |       |       | 810   |       |       |       |       | 815   |
| Arg   | Pro   | Ser   | Phe   | Ser   | Leu   | Leu   | Met   | Asp   | Met   | Leu   | Glu   | Arg   | Leu   | Pro   | Lys |
|       |       |       | 820   |       |       |       |       | 825   |       |       |       |       | 830   |       |
| Leu   | Asn   | Arg   | Arg   | Leu   | Ser   | His   | Pro   | Gly   | His   | Phe   | Trp   | Lys   | Ser   | Ala   | Asp |
|       |       | 835   |       |       |       |       | 840   |       |       |       |       | 845   |       |       |
| Ile   | Asn   | Ser   | Ser   | Lys   | Val   | Met   | Pro   | Arg   | Phe   | Glu   | Arg   | Phe   | Gly   | Leu   | Gly |
|       | 850   |       |       |       |       | 855   |       |       |       | 860   |       |       |       |       |
| Thr   | Leu   | Glu   | Ser   | Gly   | Asn   | Pro   | Lys   | Met   |       |       |       |       |       |       |
| 865   |       |       |       |       | 870   |       |       |       |       |       |       |       |       |       |

( 2 ) INFORMATION FOR SEQ ID NO:7:

( i ) SEQUENCE CHARACTERISTICS:
        ( A ) LENGTH: 2846 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

```
AGAGCAGCGC TGCGCTCGGC CGCGTTGGGA GAGAAGAAGG AGGGCGGTGG CGGGGGTGAC        60

GCGGCTATCG CGGAGGGAGG TGCAGGGGCC GCGGCCAGCC GGACACTGCA GCAGTGCGGG       120

CAGCTGCAGA AGCTCATCGA CATCTCCATC GGCAGCCTGC GCGGGCTGCG CACCAAGTGC       180

GTGGTGTCCA ACGACCTCAC CCAGCAGGAG ATACGGACCC TGGAGGCGAA GCTGGTCCGT       240

TACATTTGTA AGCAGAGGCA GTGCAAGCTG AGCGTGGCTC CCGGTGAGAG GACCCCAGAG       300

CTCAACAGCT ACCCCGCTT CAGCGACTGG CTGTACACTT TCAACGTGAG GCCGGAGGTG       360
```

```
GTGCAGGAGA TCCCCCGAGA CCTCACGCTG GATGCCCTGC TGGAGATGAA TGAGGCCAAG    420
GTGAAGGAGA CGCTGCGGCG CTGTGGGGCC AGCGGGGATG AGTGTGGCCG TCTGCAGTAT    480
GCCCTCACCT GCCTGCGGAA GGTGACAGGC CTGGGAGGGG AGCACAAGGA GGACTCCAGT    540
TGGAGTTCAT TGGATGCGCG GCGGGAAAGT GGCTCAGGGC CTTCCACGGA CACCCTCTCA    600
GCAGCCAGCC TGCCCTGGCC CCAGGGAGC  TCCCAGCTGG GCAGAGCAGG CAACAGCGCC    660
CAGGGCCCAC GCTCCATCTC CGTGTCAGCT CTTCCCGCCT CAGACTCCCC CACCCCCAGC    720
TTCAGTGAGG GCCTCTCAGA CACCTGTATT CCCTGCACG  CCAGCGGCCG GCTGACCCCC    780
CGTGCCCTGC ACAGCTTCAT CACCCCGCCC ACCACACCCC AGCTGCGACG GCACACCAAG    840
CTGAAGCCAC CACGGACGCC CCCCCCACCC AGCCGCAAGG TCTTCCAGCT GCTGCCCAGC    900
TTCCCCACAC TCACCCGGAG CAAGTCCCAT GAGTCTCAGC TGGGGAACCG CATTGATGAC    960
GTCTCCTCGA TGAGGTTTGA TCTCTCGCAT GGATCCCCAC AGATGGTACG GAGGGATATC   1020
GGGCTGTCGG TGACGCACAG GTTCTCCACC AAGTCCTGGC TGTCGCAGGT CTGCCACGTG   1080
TGCCAGAAGA GCATGATATT TGGAGTGAAG TGCAAGCATT GCAGGTTGAA GTGTCACAAC   1140
AAATGTACCA AGAAGCCCC  TGCCTGTAGA ATATCCTTCC TGCCACTAAC TCGGCTTCGG   1200
AGGACAGAAT CTGTCCCCTC GGACATCAAC AACCCGGTGG ACAGAGCAGC CGAACCCCAT   1260
TTTGGAACCC TCCCCAAAGC ACTGACAAAG AAGGAGCACC CTCCGGCCAT GAATCACCTG   1320
GACTCCAGCA GCAACCCTTC CTCCACCACC TCCTCCACAC CCTCCTCACC GGCGCCCTTC   1380
CCGACATCAT CCAACCCATC CAGCGCCACC ACGCCCCCA  ACCCCTCACC TGGCCAGCGG   1440
GACAGCAGGT TCAACTTCCC AGCTGCCTAC TTCATTCATC ATAGACAGCA GTTTATCTTT   1500
CCAGACATTT CAGCCTTTGC ACACGCAGCC CCGCTCCCTG AAGCTGCCGA CGGTACCCGG   1560
CTCGATGACC AGCCGAAAGC AGATGTGTTG GAAGCTCACG AAGCGGAGGC TGAGGAGCCA   1620
GAGGCTGGCA AGTCAGAGGC AGAAGACGAT GAGGACGAGG TGGACGACTT GCCGAGCTCT   1680
CGCCGGCCCT GGCGGGCCC  CATCTCTCGC AAGGCCAGCC AGACCAGCGT GTACCTGCAG   1740
GAGTGGGACA TCCCCTTCGA GCAGGTAGAG CTGGGCGAGC CCATCGGGCA GGGCCGCTGG   1800
GGCCGGGTGC ACCGCGGCCG CTGGCATGGC GAGGTGGCCA TTCGCCTGCT GGAGATGGAC   1860
GGCCACAACC AGGACCACCT GAAGCTCTTC AAGAAAGAGG TGATGAACTA CCGGCAGACG   1920
CGGCATGAGA ACGTGGTGCT CTTCATGGGG GCCTGCATGA ACCCGCCCCA CCTGGCCATT   1980
ATCACCAGCT TCTGCAAGGG GCGGACGTTG CACTCGTTTG TGAGGGACCC CAAGACGTCT   2040
CTGGACATCA ACAAGACGAG GCAAATCGCT CAGGAGATCA TCAAGGGCAT GGGATATCTT   2100
CATGCCAAGG GCATCGTACA CAAAGATCTC AAATCTAAGA ACGTCTTCTA TGACAACGGC   2160
AAGGTGGTCA TCACAGACTT CGGGCTGTTT GGGATCTCAG GCGTGGTCCG AGAGGGACGG   2220
CGTGAGAACC AGCTAAAGCT GTCCACGAC  TGGCTGTGCT ATCTGGCCCC TGAGATTGTA   2280
CGCGAGATGA CCCCCGGGAA GGACGAGGAT CAGCTGCCAT TCTCCAAAGC TGCTGATGTC   2340
TATGCATTTG GGACTGTTTG GTATGAGCTG CAAGCAAGAG ACTGGCCCTT GAAGAACCAG   2400
GCTGCAGAGG CATCCATCTG GCAGATTGGA AGCGGGGAAG GAATGAAGCG TGTCCTGACT   2460
TCTGTCAGCT TGGGGAAGGA AGTCAGTGAG ATCCTGTCGG CCTGCTGGGC TTTCGACCTG   2520
CAGGAGAGAC CCAGCTTCAG CCTGCTGATG GACATGCTGG AGAAACTTCC CAAGCTGAAC   2580
CGGCGGCTCT CCCACCCTGG ACACTTCTGG AAGTCAGCTG AGTTGTAGGC CTGGCTGCCT   2640
TGCATGCACC AGGGGCTTTC TTCCTCCTAA TCAACAACTC AGCACCGTGA CTTCTGCTAA   2700
AATGCAAAAT GAGATGCGGG CACTAACCCA GGGGATGCCA CCTCTGCTGC TCCAGTCGTC   2760
```

```
TCTCTCGAGG CTACTTCTTT TGCTTTGTTT TAAAAACTGG CCCTCTGCCC TCTCCACGTG      2820

GCCTGCATAT GCCCAAGCCG GAATTC                                          2846
```

( 2 ) INFORMATION FOR SEQ ID NO:8:

( i ) SEQUENCE CHARACTERISTICS:
        ( A ) LENGTH: 875 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:8:

```
Arg Ala Ala Leu Arg Ser Ala Ala Leu Gly Glu Lys Lys Glu Gly Gly
 1               5                  10                  15

Gly Gly Gly Asp Ala Ala Ile Ala Glu Gly Gly Ala Gly Ala Ala Ala
            20                  25                  30

Ser Arg Thr Leu Gln Gln Cys Gly Gln Leu Gln Lys Leu Ile Asp Ile
        35                  40                  45

Ser Ile Gly Ser Leu Arg Gly Leu Arg Thr Lys Cys Val Val Ser Asn
    50                  55                  60

Asp Leu Thr Gln Gln Glu Ile Arg Thr Leu Glu Ala Lys Leu Val Arg
65                  70                  75                  80

Tyr Ile Cys Lys Gln Arg Gln Cys Lys Leu Ser Val Ala Pro Gly Glu
                85                  90                  95

Arg Thr Pro Glu Leu Asn Ser Tyr Pro Arg Phe Ser Asp Trp Leu Tyr
            100                 105                 110

Thr Phe Asn Val Arg Pro Glu Val Val Gln Glu Ile Pro Arg Asp Leu
        115                 120                 125

Thr Leu Asp Ala Leu Leu Glu Met Asn Glu Ala Lys Val Lys Glu Thr
    130                 135                 140

Leu Arg Arg Cys Gly Ala Ser Gly Asp Glu Cys Gly Arg Leu Gln Tyr
145                 150                 155                 160

Ala Leu Thr Cys Leu Arg Lys Val Thr Gly Leu Gly Gly Glu His Lys
                165                 170                 175

Glu Asp Ser Ser Trp Ser Ser Leu Asp Ala Arg Arg Glu Ser Gly Ser
            180                 185                 190

Gly Pro Ser Thr Asp Thr Leu Ser Ala Ala Ser Leu Pro Trp Pro Pro
        195                 200                 205

Gly Ser Ser Gln Leu Gly Arg Ala Gly Asn Ser Ala Gln Gly Pro Arg
    210                 215                 220

Ser Ile Ser Val Ser Ala Leu Pro Ala Ser Asp Ser Pro Thr Pro Ser
225                 230                 235                 240

Phe Ser Glu Gly Leu Ser Asp Thr Cys Ile Pro Leu His Ala Ser Gly
                245                 250                 255

Arg Leu Thr Pro Arg Ala Leu His Ser Phe Ile Thr Pro Pro Thr Thr
            260                 265                 270

Pro Gln Leu Arg Arg His Thr Lys Leu Lys Pro Pro Arg Thr Pro Pro
        275                 280                 285

Pro Pro Ser Arg Lys Val Phe Gln Leu Leu Pro Ser Phe Pro Thr Leu
    290                 295                 300

Thr Arg Ser Lys Ser His Glu Ser Gln Leu Gly Asn Arg Ile Asp Asp
305                 310                 315                 320

Val Ser Ser Met Arg Phe Asp Leu Ser His Gly Ser Pro Gln Met Val
                325                 330                 335
```

```
Arg  Arg  Asp  Ile  Gly  Leu  Ser  Val  Thr  His  Arg  Phe  Ser  Thr  Lys  Ser
               340                      345                      350

Trp  Leu  Ser  Gln  Val  Cys  His  Val  Cys  Gln  Lys  Ser  Met  Ile  Phe  Gly
          355                      360                      365

Val  Lys  Cys  Lys  His  Cys  Arg  Leu  Lys  Cys  His  Asn  Lys  Cys  Thr  Lys
     370                      375                      380

Glu  Ala  Pro  Ala  Cys  Arg  Ile  Ser  Phe  Leu  Pro  Leu  Thr  Arg  Leu  Arg
385                      390                      395                      400

Arg  Thr  Glu  Ser  Val  Pro  Ser  Asp  Ile  Asn  Asn  Pro  Val  Asp  Arg  Ala
                    405                      410                      415

Ala  Glu  Pro  His  Phe  Gly  Thr  Leu  Pro  Lys  Ala  Leu  Thr  Lys  Lys  Glu
               420                      425                      430

His  Pro  Pro  Ala  Met  Asn  His  Leu  Asp  Ser  Ser  Ser  Asn  Pro  Ser  Ser
          435                      440                      445

Thr  Thr  Ser  Ser  Thr  Pro  Ser  Ser  Pro  Ala  Pro  Phe  Pro  Thr  Ser  Ser
     450                      455                      460

Asn  Pro  Ser  Ser  Ala  Thr  Thr  Pro  Pro  Asn  Pro  Ser  Pro  Gly  Gln  Arg
465                      470                      475                      480

Asp  Ser  Arg  Phe  Asn  Phe  Pro  Ala  Ala  Tyr  Phe  Ile  His  His  Arg  Gln
                    485                      490                      495

Gln  Phe  Ile  Phe  Pro  Asp  Ile  Ser  Ala  Phe  Ala  His  Ala  Ala  Pro  Leu
               500                      505                      510

Pro  Glu  Ala  Ala  Asp  Gly  Thr  Arg  Leu  Asp  Asp  Gln  Pro  Lys  Ala  Asp
          515                      520                      525

Val  Leu  Glu  Ala  His  Glu  Ala  Glu  Ala  Glu  Glu  Pro  Glu  Ala  Gly  Lys
     530                      535                      540

Ser  Glu  Ala  Glu  Asp  Asp  Glu  Asp  Glu  Val  Asp  Asp  Leu  Pro  Ser  Ser
545                      550                      555                      560

Arg  Arg  Pro  Trp  Arg  Gly  Pro  Ile  Ser  Arg  Lys  Ala  Ser  Gln  Thr  Ser
                    565                      570                      575

Val  Tyr  Leu  Gln  Glu  Trp  Asp  Ile  Pro  Phe  Glu  Gln  Val  Glu  Leu  Gly
               580                      585                      590

Glu  Pro  Ile  Gly  Gln  Gly  Arg  Trp  Gly  Arg  Val  His  Arg  Gly  Arg  Trp
          595                      600                      605

His  Gly  Glu  Val  Ala  Ile  Arg  Leu  Leu  Glu  Met  Asp  Gly  His  Asn  Gln
     610                      615                      620

Asp  His  Leu  Lys  Leu  Phe  Lys  Lys  Glu  Val  Met  Asn  Tyr  Arg  Gln  Thr
625                      630                      635                      640

Arg  His  Glu  Asn  Val  Val  Leu  Phe  Met  Gly  Ala  Cys  Met  Asn  Pro  Pro
                    645                      650                      655

His  Leu  Ala  Ile  Ile  Thr  Ser  Phe  Cys  Lys  Gly  Arg  Thr  Leu  His  Ser
               660                      665                      670

Phe  Val  Arg  Asp  Pro  Lys  Thr  Ser  Leu  Asp  Ile  Asn  Lys  Thr  Arg  Gln
          675                      680                      685

Ile  Ala  Gln  Glu  Ile  Ile  Lys  Gly  Met  Gly  Tyr  Leu  His  Ala  Lys  Gly
     690                      695                      700

Ile  Val  His  Lys  Asp  Leu  Lys  Ser  Lys  Asn  Val  Phe  Tyr  Asp  Asn  Gly
705                      710                      715                      720

Lys  Val  Val  Ile  Thr  Asp  Phe  Gly  Leu  Phe  Gly  Ile  Ser  Gly  Val  Val
                    725                      730                      735

Arg  Glu  Gly  Arg  Arg  Glu  Asn  Gln  Leu  Lys  Leu  Ser  His  Asp  Trp  Leu
               740                      745                      750

Cys  Tyr  Leu  Ala  Pro  Glu  Ile  Val  Arg  Glu  Met  Thr  Pro  Gly  Lys  Asp
```

|   | 755 |   |   |   |   | 760 |   |   |   |   | 765 |   |   |   |
|---|---|---|---|---|---|---|---|---|---|---|---|---|---|---|

Glu Asp Gln Leu Pro Phe Ser Lys Ala Ala Asp Val Tyr Ala Phe Gly
    770                 775             780

Thr Val Trp Tyr Glu Leu Gln Ala Arg Asp Trp Pro Leu Lys Asn Gln
785             790                 795                     800

Ala Ala Glu Ala Ser Ile Trp Gln Ile Gly Ser Gly Glu Gly Met Lys
            805             810                 815

Arg Val Leu Thr Ser Val Ser Leu Gly Lys Glu Val Ser Glu Ile Leu
            820             825                 830

Ser Ala Cys Trp Ala Phe Asp Leu Gln Glu Arg Pro Ser Phe Ser Leu
        835             840                 845

Leu Met Asp Met Leu Glu Lys Leu Pro Lys Leu Asn Arg Arg Leu Ser
    850             855             860

His Pro Gly His Phe Trp Lys Ser Ala Glu Leu
865             870             875

( 2 ) INFORMATION FOR SEQ ID NO:9:

( i ) SEQUENCE CHARACTERISTICS:
       ( A ) LENGTH: 2126 base pairs
       ( B ) TYPE: nucleic acid
       ( C ) STRANDEDNESS: double
       ( D ) TOPOLOGY: linear ( i i ) MOLECULE TYPE: cDNA ( x i ) SEQUENCE DESCRIPTION: SEQ ID NO:9:

```
GAATTCCGGC ACACATCAGC ACTCACACAG CACACAGCAC ACACACAGCA CACATCAGCG     60
CACACACAGC ACAGCTTCAT CACCCCGCCC ACCACACCCC AGCTGCGACG GCACACCAAG    120
CTGAAGCCAC CACGGACGCC CCCCCCACCC AGCCGCAAGG TCTTCCAGCT GCTGCCCAGC    180
TTCCCCACAC TCACCCGGAG CAAGTCCCAT GAGTCTCAGC TGGGGAACCG CATTGATGAC    240
GTCTCCTCGA TGAGGTTTGA TCTCTCGCAT GGATCCCCAC AGATGGTACG GAGGGATATC    300
GGGCTGTCGG TGACGCACAG GTTCTCCACC AAGTCCTGGC TGTCGCAGGT CTGCCACGTG    360
TGCCAGAAGA GCATGATATT TGGAGTGAAG TGCAAGCATT GCAGGTTGAA GTGTCACAAC    420
AAATGTACCA AAGAAGCCCC TGCCTGTAGA ATATCCTTCC TGCCACTAAC TCGGCTTCGG    480
AGGACAGAAT CTGTCCCCTC GGACATCAAC AACCCGGTGG ACAGAGCAGC CGAACCCCAT    540
TTTGGAACCC TCCCCAAAGC ACTGACAAAG AAGGAGCACC CTCCGGCCAT GAATCACCTG    600
GACTCCAGCA GCAACCCTTC CTCCACCACC TCCTCCACAC CCTCCTCACC GGCGCCCTTC    660
CCGACATCAT CCAACCCATC CAGCGCCACC ACGCCCCCA ACCCCTCACC TGGCCAGCGG    720
GACAGCAGGT TCAACTTCCC AGCTGCCTAC TTCATTCATC ATAGACAGCA GTTTATCTTT    780
CCAGACATTT CAGCCTTTGC ACACGCAGCC CCGCTCCCTG AAGCTGCCGA CGGTACCCGG    840
CTCGATGACC AGCCGAAAGC AGATGTGTTG GAAGCTCACG AAGCGGAGGC TGAGGAGCCA    900
GAGGCTGGCA AGTCAGAGGC AGAAGACGAT GAGGACGAGG TGGACGACTT GCCGAGCTCT    960
CGCCGGCCCT GGCGGGGCCC CATCTCTCGC AAGGCCAGCC AGACCAGCGT GTACCTGCAG   1020
GAGTGGGACA TCCCCTTCGA GCAGGTAGAG CTGGGCGAGC CCATCGGGCA GGGCCGCTGG   1080
GGCCGGGTGC ACCGCGGCCG CTGGCATGGC GAGGTGGCCA TTCGCCTGCT GGAGATGGAC   1140
GGCCACAACC AGGACCACCT GAAGCTCTTC AAGAAAGAGG TGATGAACTA CCGGCAGACG   1200
CGGCATGAGA ACGTGGTGCT CTTCATGGGG GCCTGCATGA ACCCGCCCCA CCTGGCCATT   1260
ATCACCAGCT TCTGCAAGGG GCGGACGTTG CACTCGTTTG TGAGGGACCC CAAGACGTCT   1320
```

-continued

| | | | | |
|---|---|---|---|---|
| CTGGACATCA | ACAAGACGAG | GCAAATCGCT | CAGGAGATCA | TCAAGGGCAT GGGATATCTT | 1380 |
| CATGCCAAGG | GCATCGTACA | CAAAGATCTC | AAATCTAAGA | ACGTCTTCTA TGACAACGGC | 1440 |
| AAGGTGGTCA | TCACAGACTT | CGGGCTGTTT | GGGATCTCAG | GCGTGGTCCG AGAGGGACGG | 1500 |
| CGTGAGAACC | AGCTAAAGCT | GTCCCACGAC | TGGCTGTGCT | ATCTGGCCCC TGAGATTGTA | 1560 |
| CGCGAGATGA | CCCCCGGGAA | GGACGAGGAT | CAGCTGCCAT | TCTCCAAAGC TGCTGATGTC | 1620 |
| TATGCATTTG | GGACTGTTTG | GTATGAGCTG | CAAGCAAGAG | ACTGGCCCTT GAAGAACCAG | 1680 |
| GCTGCAGAGG | CATCCATCTG | GCAGATTGGA | AGCGGGGAAG | GAATGAAGCG TGTCCTGACT | 1740 |
| TCTGTCAGCT | TGGGGAAGGA | AGTCAGTGAG | ATCCTGTCGG | CCTGCTGGGC TTTCGACCTG | 1800 |
| CAGGAGAGAC | CCAGCTTCAG | CCTGCTGATG | GACATGCTGG | AGAAACTTCC CAAGCTGAAC | 1860 |
| CGGCGGCTCT | CCCACCCTGG | ACACTTCTGG | AAGTCAGCTG | AGTTGTAGGC CTGGCTGCCT | 1920 |
| TGCATGCACC | AGGGGCTTTC | TTCCTCCTAA | TCAACAACTC | AGCACCGTGA CTTCTGCTAA | 1980 |
| AATGCAAAAT | GAGATGCGGG | CACTAACCCA | GGGGATGCCA | CCTCTGCTGC TCCAGTCGTC | 2040 |
| TCTCTCGAGG | CTACTTCTTT | TGCTTTGTTT | TAAAAACTGG | CCCTCTGCCC TCTCCACGTG | 2100 |
| GCCTGCATAT | GCCCAAGCCG | GAATTC | | | 2126 |

( 2 ) INFORMATION FOR SEQ ID NO:10:

( i ) SEQUENCE CHARACTERISTICS:
        ( A ) LENGTH: 635 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:10:

```
Glu Phe Arg His Thr Ser Ala Leu Thr Gln His Thr Ala His Thr Gln
 1               5                  10                  15

His Thr Ser Ala His Thr Gln His Ser Phe Ile Thr Pro Pro Thr Thr
            20                  25                  30

Pro Gln Leu Arg Arg His Thr Lys Leu Lys Pro Pro Arg Thr Pro Pro
        35                  40                  45

Pro Pro Ser Arg Lys Val Phe Gln Leu Leu Pro Ser Phe Pro Thr Leu
    50                  55                  60

Thr Arg Ser Lys Ser His Glu Ser Gln Leu Gly Asn Arg Ile Asp Asp
65                  70                  75                  80

Val Ser Ser Met Arg Phe Asp Leu Ser His Gly Ser Pro Gln Met Val
                85                  90                  95

Arg Arg Asp Ile Gly Leu Ser Val Thr His Arg Phe Ser Thr Lys Ser
            100                 105                 110

Trp Leu Ser Gln Val Cys His Val Cys Gln Lys Ser Met Ile Phe Gly
        115                 120                 125

Val Lys Cys Lys His Cys Arg Leu Lys Cys His Asn Lys Cys Thr Lys
    130                 135                 140

Glu Ala Pro Ala Cys Arg Ile Ser Phe Leu Pro Leu Thr Arg Leu Arg
145                 150                 155                 160

Arg Thr Glu Ser Val Pro Ser Asp Ile Asn Asn Pro Val Asp Arg Ala
                165                 170                 175

Ala Glu Pro His Phe Gly Thr Leu Pro Lys Ala Leu Thr Lys Lys Glu
            180                 185                 190

His Pro Pro Ala Met Asn His Leu Asp Ser Ser Ser Asn Pro Ser Ser
        195                 200                 205
```

```
Thr Thr Ser Ser Thr Pro Ser Pro Ala Pro Phe Pro Thr Ser Ser
    210             215             220
Asn Pro Ser Ser Ala Thr Thr Pro Pro Asn Pro Ser Pro Gly Gln Arg
225             230             235                         240
Asp Ser Arg Phe Asn Phe Pro Ala Ala Tyr Phe Ile His His Arg Gln
                245             250                         255
Gln Phe Ile Phe Pro Asp Ile Ser Ala Phe Ala His Ala Ala Pro Leu
                260             265             270
Pro Glu Ala Ala Asp Gly Thr Arg Leu Asp Asp Gln Pro Lys Ala Asp
            275             280             285
Val Leu Glu Ala His Glu Ala Glu Ala Glu Glu Pro Glu Ala Gly Lys
    290             295             300
Ser Glu Ala Glu Asp Asp Glu Asp Glu Val Asp Asp Leu Pro Ser Ser
305             310             315                         320
Arg Arg Pro Trp Arg Gly Pro Ile Ser Arg Lys Ala Ser Gln Thr Ser
                325             330             335
Val Tyr Leu Gln Glu Trp Asp Ile Pro Phe Glu Gln Val Glu Leu Gly
            340             345             350
Glu Pro Ile Gly Gln Gly Arg Trp Gly Arg Val His Arg Gly Arg Trp
        355             360             365
His Gly Glu Val Ala Ile Arg Leu Leu Glu Met Asp Gly His Asn Gln
    370             375             380
Asp His Leu Lys Leu Phe Lys Lys Glu Val Met Asn Tyr Arg Gln Thr
385             390             395                         400
Arg His Glu Asn Val Val Leu Phe Met Gly Ala Cys Met Asn Pro Pro
                405             410             415
His Leu Ala Ile Ile Thr Ser Phe Cys Lys Gly Arg Thr Leu His Ser
            420             425             430
Phe Val Arg Asp Pro Lys Thr Ser Leu Asp Ile Asn Lys Thr Arg Gln
        435             440             445
Ile Ala Gln Glu Ile Ile Lys Gly Met Gly Tyr Leu His Ala Lys Gly
    450             455             460
Ile Val His Lys Asp Leu Lys Ser Lys Asn Val Phe Tyr Asp Asn Gly
465             470             475                         480
Lys Val Val Ile Thr Asp Phe Gly Leu Phe Gly Ile Ser Gly Val Val
                485             490             495
Arg Glu Gly Arg Arg Glu Asn Gln Leu Lys Leu Ser His Asp Trp Leu
            500             505             510
Cys Tyr Leu Ala Pro Glu Ile Val Arg Glu Met Thr Pro Gly Lys Asp
        515             520             525
Glu Asp Gln Leu Pro Phe Ser Lys Ala Ala Asp Val Tyr Ala Phe Gly
    530             535             540
Thr Val Trp Tyr Glu Leu Gln Ala Arg Asp Trp Pro Leu Lys Asn Gln
545             550             555                         560
Ala Ala Glu Ala Ser Ile Trp Gln Ile Gly Ser Gly Glu Gly Met Lys
                565             570             575
Arg Val Leu Thr Ser Val Ser Leu Gly Lys Glu Val Ser Glu Ile Leu
            580             585             590
Ser Ala Cys Trp Ala Phe Asp Leu Gln Glu Arg Pro Ser Phe Ser Leu
        595             600             605
Leu Met Asp Met Leu Glu Lys Leu Pro Lys Leu Asn Arg Arg Leu Ser
    610             615             620
His Pro Gly His Phe Trp Lys Ser Ala Glu Leu
625             630             635
```

( 2 ) INFORMATION FOR SEQ ID NO:11:

( i ) SEQUENCE CHARACTERISTICS:
        ( A ) LENGTH: 326 amino acids
        ( B ) TYPE: amino acid
        ( C ) STRANDEDNESS: Not Relevant
        ( D ) TOPOLOGY: Not Relevant ( i i ) MOLECULE TYPE: peptide ( x i ) SEQUENCE DESCRIPTION: SEQ ID NO:11:

```
Asp Ala Lys Ser Ser Glu Glu Asn Trp Asn Ile Leu Ala Glu Glu Ile
 1               5                  10                  15
Leu Ile Gly Pro Arg Ile Gly Ser Gly Ser Phe Gly Thr Val Tyr Arg
                20                  25                  30
Ala His Trp His Gly Pro Val Pro Val Lys Thr Leu Asn Val Lys Thr
            35                  40                  45
Pro Ser Pro Ala Gln Leu Gln Ala Phe Lys Asn Glu Val Ala Met Leu
50                  55                  60
Lys Lys Thr Arg His Cys Asn Ile Leu Ile Phe Met Gly Cys Val Ser
65                  70                  75                  80
Lys Pro Ser Leu Ala Ile Val Thr Gln Trp Cys Glu Gly Ser Ser Leu
                85                  90                  95
Tyr Lys His Val His Val Ser Glu Thr Lys Phe Lys Leu Asn Thr Leu
            100                 105                 110
Ile Asp Ile Gly Arg Gln Val Ala Gln Gln Met Asp Tyr Leu His Ala
        115                 120                 125
Lys Asn Ile Ile His Arg Asp Leu Lys Ser Asn Asn Ile Phe Leu His
130                 135                 140
Glu Asp Leu Ser Val Lys Ile Gly Asp Phe Gly Leu Ala Thr Ala Lys
145                 150                 155                 160
Thr Arg Trp Ser Gly Glu Lys Gln Ala Asn Gln Pro Thr Gly Ser Ile
                165                 170                 175
Leu Trp Met Ala Pro Glu Val Ile Arg Met Gln Glu Leu Asn Pro Tyr
            180                 185                 190
Ser Phe Gln Ser Asp Val Tyr Ala Phe Gly Ile Val Met Tyr Glu Leu
        195                 200                 205
Leu Ala Glu Cys Leu Pro Tyr Gly His Ile Ser Asn Lys Asp Gln Ile
210                 215                 220
Leu Phe Met Val Gly Arg Gly Leu Leu Arg Pro Asp Met Ser Gln Val
225                 230                 235                 240
Arg Ser Asp Ala Arg Arg His Ser Lys Arg Ile Ala Glu Asp Cys Ile
                245                 250                 255
Lys Tyr Thr Pro Lys Asp Arg Pro Leu Phe Arg Pro Leu Leu Trp Met
            260                 265                 270
Leu Glu Asn Met Leu Arg Thr Leu Pro Lys Ile His Arg Ser Ala Ser
        275                 280                 285
Glu Pro Asn Leu Thr Gln Ser Gln Leu Gln Asn Asp Glu Phe Leu Tyr
290                 295                 300
Leu Pro Ser Pro Lys Thr Pro Val Asn Phe Asn Asn Phe Gln Phe Phe
305                 310                 315                 320
Gly Ser Ala Gly Asn Ile
                325
```

( 2 ) INFORMATION FOR SEQ ID NO:12:

(i) SEQUENCE CHARACTERISTICS:
  (A) LENGTH: 315 amino acids
  (B) TYPE: amino acid
  (C) STRANDEDNESS: Not Relevant
  (D) TOPOLOGY: Not Relevant (ii) MOLECULE TYPE: peptide (xi) SEQUENCE DESCRIPTION: SEQ ID NO:12:

```
Gly Gln Arg Asp Ser Ser Tyr Tyr Trp Glu Ile Glu Ala Ser Glu Val
  1               5                  10                  15
Met Leu Ser Thr Arg Ile Gly Ser Gly Ser Phe Gly Thr Val Tyr Lys
             20                  25                  30
Cys Lys Trp His Gly Asp Val Ala Val Lys Ile Leu Lys Val Val Asp
         35                  40                  45
Pro Thr Pro Glu Gln Phe Gln Ala Phe Arg Asn Glu Val Ala Val Leu
     50                  55                  60
Arg Lys Thr Arg His Val Asn Ile Leu Leu Phe Met Gly Tyr Met Thr
 65              70                  75                  80
Lys Asp Asn Leu Ala Ile Val Thr Gln Trp Cys Glu Gly Ser Ser Leu
                 85                  90                  95
Tyr Lys His Leu His Val Gln Glu Thr Lys Phe Gln Met Phe Gln Leu
             100                 105                 110
Ile Asp Ile Ala Arg Gln Thr Ala Gln Gly Met Asp Tyr Leu His Ala
         115                 120                 125
Lys Asn Ile Ile His Arg Asp Met Lys Ser Asn Asn Ile Phe Leu His
     130                 135                 140
Glu Gly Leu Thr Val Lys Ile Gly Asp Phe Gly Leu Ala Thr Val Lys
145                 150                 155                 160
Ser Arg Trp Ser Gly Ser Gln Gln Val Glu Gln Pro Thr Gly Ser Val
                 165                 170                 175
Leu Trp Met Ala Pro Glu Val Ile Arg Met Gln Asp Asn Asn Pro Phe
             180                 185                 190
Ser Phe Gln Ser Asp Val Tyr Ser Tyr Gly Ile Val Leu Tyr Glu Leu
         195                 200                 205
Met Thr Gly Glu Leu Pro Tyr Ser His Ile Asn Asn Arg Asp Gln Ile
     210                 215                 220
Ile Phe Met Val Gly Arg Gly Tyr Ala Ser Pro Asp Leu Ser Lys Leu
225                 230                 235                 240
Tyr Lys Asn Cys Pro Lys Ala Met Lys Arg Leu Val Ala Asp Cys Val
             245                 250                 255
Lys Lys Val Lys Glu Glu Arg Pro Leu Phe Pro Gln Ile Leu Ser Ser
         260                 265                 270
Ile Glu Leu Leu Gln His Ser Leu Pro Lys Ile Asn Arg Ser Ala Ser
     275                 280                 285
Glu Pro Ser Leu His Arg Ala Ala His Thr Glu Asp Ile Asn Ala Cys
     290                 295                 300
Thr Leu Thr Thr Ser Pro Arg Leu Pro Val Phe
305                 310                 315
```